United States Patent
Annoni et al.

(10) Patent No.: US 10,667,747 B2
(45) Date of Patent: Jun. 2, 2020

(54) METHOD AND APPARATUS FOR PAIN CONTROL USING BAROREFLEX SENSITIVITY DURING POSTURE CHANGE

(71) Applicant: Boston Scientific Neuromodulation Corporation, Valencia, CA (US)

(72) Inventors: Elizabeth Mary Annoni, White Bear Lake, MN (US); Pramodsingh Hirasingh Thakur, Woodbury, MN (US); Bryan Allen Clark, Forest Lake, MN (US); Kyle Harish Srivastava, Saint Paul, MN (US); Jianwen Gu, Valencia, CA (US); James John Kleinedler, Plymouth, MN (US); David J. Ternes, Roseville, MN (US); David L. Perschbacher, Coon Rapids, MN (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 207 days.

(21) Appl. No.: 15/788,403

(22) Filed: Oct. 19, 2017

(65) Prior Publication Data

US 2018/0110464 A1    Apr. 26, 2018

Related U.S. Application Data

(60) Provisional application No. 62/451,455, filed on Jan. 27, 2017, provisional application No. 62/412,587, filed on Oct. 25, 2016.

(51) Int. Cl.
*A61N 1/34* (2006.01)
*A61B 5/00* (2006.01)
(Continued)

(52) U.S. Cl.
CPC ............ *A61B 5/4824* (2013.01); *A61B 5/021* (2013.01); *A61B 5/0205* (2013.01);
(Continued)

(58) Field of Classification Search
None
See application file for complete search history.

(56) References Cited

U.S. PATENT DOCUMENTS

| 4,297,685 A | 10/1981 | Brainard, II |
| 5,187,675 A | 2/1993 | Dent et al. |

(Continued)

FOREIGN PATENT DOCUMENTS

| EP | 1897586 A1 | 3/2008 |
| RU | 2559783 C1 | 8/2015 |

(Continued)

OTHER PUBLICATIONS

"2015 Sleep in America® Poll Sleep and Pain—Summary of Findings", National Sleep Foundation, (2015), 1-54.
(Continued)

*Primary Examiner* — Kennedy Schaetzle
(74) *Attorney, Agent, or Firm* — Schwegman Lundberg & Woessner, P.A.

(57) ABSTRACT

An example of a system for providing a patient with pain management includes a pain monitoring circuit. The pain monitoring circuit may include parameter analyzer circuitry and pain score generator circuitry. The parameter analyzer circuitry may be configured to receive and analyze one or more timing parameters and one or more baroreflex parameters allowing for determination of baroreflex sensitivity (BRS) of the patient. The one or more timing parameters are indicative of time intervals during which values of the one or more baroreflex parameters are used to determine the BRS. The pain score generator circuitry may be configured
(Continued)

to compute a pain score using an outcome of the analysis. The pain score is a function of the BRS during the time intervals and indicative of a degree of pain of the patient.

20 Claims, 9 Drawing Sheets

(51) Int. Cl.
    *A61N 1/36*     (2006.01)
    *A61B 5/0205*     (2006.01)
    *A61B 5/021*     (2006.01)
    *A61B 5/08*     (2006.01)
    *A61B 5/11*     (2006.01)
    *A61B 5/024*     (2006.01)

(52) U.S. Cl.
    CPC .......... *A61B 5/0816* (2013.01); *A61B 5/1116* (2013.01); *A61B 5/1118* (2013.01); *A61B 5/7282* (2013.01); *A61N 1/36021* (2013.01); *A61N 1/36071* (2013.01); *A61N 1/36139* (2013.01); *A61B 5/024* (2013.01); *A61B 5/02405* (2013.01); *A61N 1/36062* (2017.08)

(56) References Cited

U.S. PATENT DOCUMENTS

| | | | |
|---|---|---|---|
| 5,774,591 A | 6/1998 | Black et al. | |
| 6,016,103 A | 1/2000 | Leavitt | |
| 6,076,011 A | 6/2000 | Hoover | |
| 6,088,040 A | 7/2000 | Oda et al. | |
| 6,173,260 B1 | 1/2001 | Slaney | |
| 6,480,734 B1 | 11/2002 | Zhang et al. | |
| 6,497,658 B2 | 12/2002 | Roizen et al. | |
| 6,654,632 B2 | 11/2003 | Lange et al. | |
| 6,659,968 B1 | 12/2003 | McClure | |
| 6,731,984 B2 | 5/2004 | Cho et al. | |
| 6,871,099 B1 | 3/2005 | Whitehurst et al. | |
| 7,001,337 B2 | 2/2006 | Dekker | |
| 7,004,907 B2 | 2/2006 | Banet et al. | |
| 7,177,686 B1 | 2/2007 | Turcott | |
| 7,189,204 B2 | 3/2007 | Ni et al. | |
| 7,222,075 B2 | 5/2007 | Petrushin | |
| 7,299,086 B2 | 11/2007 | McCabe et al. | |
| 7,376,457 B2 | 5/2008 | Ross | |
| 7,407,485 B2 | 8/2008 | Huiku | |
| 7,463,927 B1 | 12/2008 | Chaouat | |
| 7,566,308 B2 | 7/2009 | Stahmann | |
| 7,627,475 B2 | 12/2009 | Petrushin | |
| 7,636,602 B2 | 12/2009 | Baru Fassio et al. | |
| 7,650,184 B2 | 1/2010 | Walter | |
| 7,678,061 B2 | 3/2010 | Lee et al. | |
| 7,775,993 B2 | 8/2010 | Heruth et al. | |
| 7,957,809 B2 | 6/2011 | Bourget et al. | |
| 7,986,991 B2 | 7/2011 | Prichep | |
| 8,019,439 B2 | 9/2011 | Kuzma et al. | |
| 8,055,348 B2 | 11/2011 | Heruth et al. | |
| 8,083,682 B2 | 12/2011 | Dalal et al. | |
| 8,192,376 B2 | 6/2012 | Lovett et al. | |
| 8,209,182 B2 | 6/2012 | Narayanan | |
| 8,290,596 B2 | 10/2012 | Wei et al. | |
| 8,332,038 B2 | 12/2012 | Heruth et al. | |
| 8,398,556 B2 | 3/2013 | Sethi et al. | |
| 8,447,401 B2 | 5/2013 | Miesel et al. | |
| 8,475,370 B2 | 7/2013 | McCombie et al. | |
| 8,529,459 B2 | 9/2013 | Malker et al. | |
| 8,606,356 B2 | 12/2013 | Lee et al. | |
| 8,688,221 B2 | 4/2014 | Miesel | |
| 8,744,587 B2 | 6/2014 | Miesel et al. | |
| 8,805,518 B2 | 8/2014 | King et al. | |
| 9,066,659 B2 | 6/2015 | Thakur et al. | |
| 9,072,870 B2 | 7/2015 | Wu et al. | |
| 9,119,965 B2 | 9/2015 | Xi et al. | |
| 9,314,168 B2 | 4/2016 | Watson et al. | |
| 9,395,792 B1 | 7/2016 | Kahn et al. | |
| 2004/0015091 A1 | 1/2004 | Greenwald et al. | |
| 2005/0209643 A1 | 9/2005 | Heruth et al. | |
| 2007/0167859 A1 | 7/2007 | Finneran et al. | |
| 2007/0213783 A1 | 9/2007 | Pless | |
| 2007/0260285 A1 | 11/2007 | Libbus et al. | |
| 2008/0177191 A1 | 7/2008 | Patangay et al. | |
| 2008/0249430 A1 | 10/2008 | John et al. | |
| 2009/0192556 A1 | 7/2009 | Wu et al. | |
| 2009/0312663 A1 | 12/2009 | John et al. | |
| 2009/0318986 A1 | 12/2009 | Alo et al. | |
| 2010/0016913 A1 | 1/2010 | Arcot-Krishnamurthy et al. | |
| 2010/0286549 A1 | 11/2010 | John et al. | |
| 2011/0015702 A1 | 1/2011 | Ternes et al. | |
| 2011/0021928 A1 | 1/2011 | Giovangrandi et al. | |
| 2011/0124979 A1 | 5/2011 | Heneghan et al. | |
| 2011/0137134 A1 | 6/2011 | Hemmerling et al. | |
| 2011/0172562 A1 | 7/2011 | Sahasrabudhe et al. | |
| 2011/0224749 A1 | 9/2011 | Ben-David et al. | |
| 2011/0306846 A1 | 12/2011 | Osorio | |
| 2013/0165994 A1 | 6/2013 | Ternes et al. | |
| 2013/0268016 A1 | 10/2013 | Xi et al. | |
| 2014/0276188 A1 | 9/2014 | Jardin | |
| 2014/0276549 A1* | 9/2014 | Osorio | A61M 5/1723 604/503 |
| 2015/0005842 A1 | 1/2015 | Lee et al. | |
| 2015/0289803 A1 | 10/2015 | Wu et al. | |
| 2016/0022203 A1 | 1/2016 | Arnold et al. | |
| 2016/0082265 A1 | 3/2016 | Moffitt et al. | |
| 2016/0129272 A1 | 5/2016 | Hou et al. | |
| 2016/0144194 A1 | 5/2016 | Roothans et al. | |
| 2016/0243359 A1 | 8/2016 | Sharma | |
| 2016/0302720 A1 | 10/2016 | John et al. | |
| 2016/0350509 A1 | 12/2016 | Sharma | |
| 2016/0374567 A1 | 12/2016 | Breslow et al. | |
| 2018/0078768 A1 | 3/2018 | Thakur et al. | |
| 2018/0085055 A1 | 3/2018 | Annoni et al. | |
| 2018/0085584 A1 | 3/2018 | Thakur et al. | |
| 2018/0192941 A1 | 7/2018 | Annoni et al. | |
| 2018/0192942 A1 | 7/2018 | Clark et al. | |
| 2018/0193644 A1 | 7/2018 | Annoni et al. | |
| 2018/0193650 A1 | 7/2018 | Srivastava et al. | |
| 2018/0193651 A1 | 7/2018 | Annoni et al. | |
| 2018/0193652 A1 | 7/2018 | Srivastava et al. | |
| 2018/0229040 A1 | 8/2018 | Srivastava et al. | |

FOREIGN PATENT DOCUMENTS

| | | |
|---|---|---|
| WO | WO-2007007058 A1 | 1/2007 |
| WO | WO-2009055127 A1 | 4/2009 |
| WO | WO-2010051406 A1 | 5/2010 |
| WO | WO-2011008747 A2 | 1/2011 |
| WO | WO-2011053607 A1 | 5/2011 |
| WO | WO-2013134479 A1 | 9/2013 |
| WO | WO-2014151860 A1 | 9/2014 |
| WO | WO-2015060888 A1 | 4/2015 |
| WO | WO-2015128567 | 9/2015 |
| WO | WO-2016077786 A1 | 5/2016 |
| WO | WO-2018052695 A1 | 3/2018 |
| WO | WO-2018063637 A1 | 4/2018 |
| WO | WO-2018063912 A1 | 4/2018 |
| WO | WO-2018080887 A1 | 5/2018 |

OTHER PUBLICATIONS

Ahern, David K., et al., "Comparison of lumbar paravertebral EMG patterns in chronic low back pain patients and non-patient controls", Pain, 34, (1988), 153-160.

Allum, John H.J., et al., "A speedy solution for balance and gait analysis: angular velocity measured at the centre of body mass", Current Opinion in Neurology 18, (2005), 15-21.

Alo, Kenneth M., et al., "Effect of Spinal Cord Stimulation on Sensory Nerve Conduction Threshold Functional Measures", Neuromodulation, vol. 3, No. 3, (2000), 145-154.

Annoni, Elizabeth M., et al., "Method and Apparatus for Pain Management Using Objective Pain Measure", U.S. Appl. No. 62/400,336, filed Sep. 27, 2016.

(56) References Cited

OTHER PUBLICATIONS

Arsenault, Marianne, et al., "Pain Modulation Induced by Respiration: Phase and Frequency Effects", Neuroscience 252, (2013), 501-511.

Artner, Juraj, et al., "Prevalence of sleep deprivation in patients with chronic neck and back pain: a retrospective evaluation of 1016 patients", Journal of Pain Research: 6, (2013), 1-6.

Bakker, Jorn, et al., "What's your current stress level? Detection of stress patterns from GSR sensor data", Eindhoven University of Technology—The Netherlands, (2011), 1-8.

Baliki, Marwan N., et al., "Beyond Feeling: Chronic Pain hurts the Brain, Disrupting the Default-Mode Network Dynamics", The Journal of Neuroscience, 28 (6), (Feb. 6, 2008), 1398-1403.

Banos, Oresti, et al., "PhysioDroid: Combining Wearable Health Sensors and Mobile Devices for a Ubiquitous, Continuous, and Personal Monitoring", The Scientific World Journal, vol. 2014 Article ID 190824, (2014), 11 pgs.

Barad, Meredith J., et al., "Complex Regional Pain Syndrome Is Associated With Structural Abnormalities in Pain-Related Regions of the Human Brain", The Journal of Pain, vol. 15, No. 2, (Feb. 2914), 197-203.

Barkley, Jacob E., et al., "The effect of spinal cord stimulation unit revision on perceived pain, anxiety, mobility and physical activity in individuals with low back/lower extremity pain", Kent State University—The Spine and Pain Institute, Presented at Annual Meeting of the North American Neuromodulation Society (NANS) on Dec. 11-14, 2014, 1 pg.

Beneck, George J., et al., "Spectral analysis of EMG using intramuscular electrodes reveals non-linear fatigability characteristics in persons with chronic low back pain", Journal of Electromyography and Kinesiology 23, (2013), 70-77.

Ben-Israel, Nir, et al., "Monitoring the nociception level: a multiparameter approach", J Clin Monit Comput, (Jul. 2012), 10 pgs.

Ben-Israel, Nir, et al., "Monitoring the nociception level: a multiparameter approach", J Clin Monit Comput 27, (2013), 659-668.

Boselli, E., et al., "Prediction of immediate postoperative pain using the analgesia/nociception index: a prospective observational study", British Journal of Anaesthesia 112 (4):, (2014), 715-721.

Boselli, E., et al., "Prospective observational study of the non-invasive assessment of immediate postoperative pain using the analgesia/nociception index (ANI)", British Journal of Anaesthesia 111, (2013), 453-459.

Broucqsault-Dédrie, Celine, et al., "Measurement of Heart Rate Variability to Assess Pain in Sedated Critically Ill Patients: A Prospective Observational Study", PLOS One, (Jan. 25, 2016), 1-11.

Chan, C. W.Y., et al., "Subjective pain sensation is linearly correlated with the Flexion reflex in man", Brain Research, 479, (1989), 145-150.

Chapman, C. Richard, et al., "Phasic pupil dilation response to noxious stimulation in normal volunteers: relationship to brain evoked potentials and pain report", (1999), 44-52.

Cheng, Qian, et al., "GaitTrack: Health Monitoring of Body Motion from Spatio-Temporal Parameters of Simple Smart Phones", The ACM Conference on Bioinformatics, Computational Biology, Biomed Biomedical Informatics (BCB) Health Information Symposium (HIS), Sep. 25, 2013,, (2013), 1-10.

Chuang, Chiung-Cheng, et al., "Photoplethysmography variability as an alternative approach to obtain heart rate variability information in chronic pain patient", J Clin Monit Comput—Published online, (Feb. 24, 2015), 1-6.

Chung, Ok Y., "Baroreflex sensitivity associated hypoalgesia in healthy states is altered by chronic pain", Pain 138, (2008), 87-97.

Ciampi De Andrade, Daniel, et al., "Neurophysiological assessment of spinal cord stimulation in failed back surgery syndrome", Pain 150, (2010), 485-491.

Cinaz, Burcu, et al., "Monitoring of mental workload levels during an everyday life office-work scenario", Pers Ubiquit Comput 17, (2013), 229-239.

Culic, Ognjen, et al., "Serum activities of adenosine deaminase, dipeptidyl peptidase IV and prolyl endopeptidase in patients with fibromyalgia:diagnostic implications", Clin Rheumatol 35, (2016), 2565-2571.

Dansie, Elizabeth J., et al., "Activity in Adults with Chronic Widespread Pain", The Journal of Pain—Accepted Manuscript, (2014), 33 pgs.

Davydov, Dmitry M., et al., "Cardiovascular activity and chronic pain severity", Physiology & Behavior 152, 203-216 (2015).

De-La-Herran, Alvaro M., et al., "Gait Analysis Methods: An Overview of Wearable and Non-Wearable Systems, Highlighting Clinical Applications", Sensors 14, (2014), 3362-3394.

Denk, Franziska, et al., "Chronic Pain: Emerging Evidence for the Involvement of Epigenetics", Neuron 73 (3), (2012), 435-444.

Duschek, S., "Relationship between baroreceptor cardiac reflex sensitivity and pain experience in normotensive individuals", International Journal of Psychophysiology 65, (2007), 193-200.

Eisenberg, Elon, et al., "Quantitative Sensory Testing for Spinal Cord Stimulation in Patients With Chronic Neuropathic Pain", (2006), 161-165.

Evans, Subhadr, et al., "Heart rate variability as a biomarker for autonomic nervous system response differences between children with chronic pain and healthy control children", Journal of Pain Research 3.6, (2013), 449-457.

Fazalbhoy, Azharuddin, et al., "Individual differences in the cardiovascular responses to tonic muscle pain: parallel increases or decreases in muscle sympathetic nerve activity, blood pressure and heart rate", Exp Physiol 97.10, (2012), 1084-1092.

Geisser, Michael E., et al., "Pain-Related Fear, Lumbar Flexion, and Dynamic EMG Among Persons With Chronic Musculoskeletal Low Back Pain", Clin J Pain, vol. 20, No. 2, (Apr. 2004).

Generaal, Ellen, et al., "Reduced hypothalamic-pituitary-adrenal axis activity in chronic multi-site musculoskeletal pain: partly masked by depressive and anxiety disorders", BMC Musculoskeletal Disorders, 15:227, (2014), 1-11.

Gouveia, S., et al., "Assessing Baroreflex Sensitivity in the Sequences Technique: Local versus Global Approach", Computers in Cardiology, 32, (2005), 279-282.

Granovsky, Yelena, et al., "Objective Correlate of Subjective Pain Perception by Contact Heat-Evoked Potentials", The Journal of Pain, vol. 9, No. 1, (Jan. 2008), 53-63.

Green, Alexande L., "Measurement of muscle sympathetic nerve activity reveals true sympathetic changes in chronic pain", Exp Physiol 97.10, (2012), 1083.

Hallman, David, et al., "Autonomic regulation, physical activity and perceived stress in subjects with musculoskeletal pain: 24-hour ambulatory monitoring", International Journal of Psychophysiology 86, (2012), 276-282.

Hallman, David M., et al., "Changes in physical activity and heart rate variability in chronic neck-shoulder pain: monitoring during work and leisure time", Int Arch Occup Environ Health 87, (2014), 735-744.

Hallman, David M., et al., "Long-Term Monitoring of Physical Behavior Reveals Different Cardiac Responses to Physical Activity among Subjects with and without Chronic Neck Pain", BioMed Research International, vol. 2015, Article ID 907482, 11 pages, http://dx.doi.org/10.1155/2015/907482, 11 pages.

Hartwich, Doreen, et al., "Effect of muscle metaboreflex activation on spontaneous cardiac baroreflex sensitivity during exercise in humans", J Physiol 589.24, (2011), 6157-6171.

Jess, Gunnar, et al., "Monitoring heart rate variability to assess experimentally induced pain using the analgesia nociception index—A randomised volunteer study", Eur J Anaesthesiol 32, (2015), 1-8.

Kang, Jon-Eun, et al., "Pulse transit time shows vascular changes caused by propofol in children", J Clin Monit Comput 29, (2015), 533-537.

Keefe, Francis J,, et al., "An Objective Approach to Quantifing Pain Behavior and Gait Patterns in Low Back Pain Patients", Pain, 21, (1985), 153-161.

Kemler, Marius A., et al., "Impact of Spinal Cord Stimulation on Sensory Characteristics in Complex Regional Pain Syndrome Type 1—A Randomized Trial", Anesthesiology, 95, (2001), 72-80.

(56) References Cited

OTHER PUBLICATIONS

Keshari, Kayvan R., et al., "Lactic Acid and Proteoglycans as Metabolic Markers dor Discogenic Back Pain", SPINE, vol. 13, No. 3, (2008), 312-317.
Kim, Young Uk, et al., "Pulse Transit Time as a Predictor of the Efficacy of a Celiac Plexus Block in Patients With Chronic Intractable Abdominal Pain", Clin J Pain, vol. 32, No. 6, (Jun. 2015), 522-526.
Kodituwakku, Sandun, et al., "Point Process Respiratory Sinus Arrhythmia Analysis during Deep Tissue Pain Stimulation", Computing in Cardiology 38, (2011), 193-196.
Koenig, J., et al., "Heart rate variability and experimentally induced pain in healthy adults: A systematic review", European Journal of Pain 18, (2014), 301-314.
Koenig, Julian, et al., "Chronic Pain and Heart Rate Variability in a Cross-Sectional Occupational Sample Evidence for Impaired Vagal Control", The Clinical Journal of Pain, Publish Ahead of Print, (2015), 31 pgs.
La Rovere, Maria Teresa, et al., "Baroreflex Sensitivity: Measurement and Clinical Implications", Ann Noninvasive Electrodardiol, 13(2):191-207, 2008.
Lamoth, Claudine J.C., et al., "How do persons with chronic low back pain speed up and slow down? Trunk-pelvis coordination and erector spinae activity during gait", Gait & Posture 23, (2006), 230-239.
Lamoth, Claudine J.C., et al., "Pelvis-Thorax Coordination in the Transverse Plane During Walking in Persons With Nonspecific Low Back Pain", SPINE, vol. 27, No. 4, (2002), E92-E99.
Lane, James D., et al., "Respiratory Sinus Arrhythmia and Cardiovascular Responses to Stress", Psychophysiology, vol. 29, No. 4, (1992), 461-470.
Latremoliere, Alban, et al., "Reduction of Neuropathic and Inflammatory Pain through Inhibition of the Tetrahydrobiopterin Pathway", Neuron, 86 (6), (2015), 1393-1406.
Ledowski, Thomas, et al., "The influence of age and sex on the relationship between heart rate variability, haemodynamic variables and subjective measures of acute post-operative pain", European Journal of Anaesthesiology, vol. 28, No. 6, (2011), 433-437.
Lee, Jihyoung, et al., "Validation of normalized pulse volume in the outer ear as a simple measure of sympathetic activity using warm and cold pressor tests: towards applications in ambulatory monitoring", Physiol. Meas. 34, (2013), 359-375.
Lidberg, Lars, et al., "Sympathetic Skin Nerve Dischai gcs in Relation lo Anipliliule of Skin Resistance Responses", Psychophysiology, vol. 18, No. 3, (May 1981), 268-270.
Logier, R., et al., "PhysioDoloris: a monitoring device for Analgesia / Nociception balance evaluation using Heart Rate Variability analysis", 32nd Annual International Conference of the IEEE EMBS, (2010), 1194-1197.
Marchi, Antonio, et al., "Pain Biomarkers", Clin Drug Invest, 29 Suppl 1, (2009), 41-46.
Martini, Chris H., et al., "Ability of the Nociception Level, a Multiparameter Composite of Autonomic Signals, to Detect Noxious Stimuli during Propofol-Remifentanil Anesthesia", Anesthesiology, vol. 123, No. 3, (2015), 524-534.
Mauer, C,, et al., "Quantitative sensory testing in the German Research Network on Neuropathic Pain (DFNS): Somatosensory abnormalities in 1236 patients with different neuropathic pain syndromes", Pain 150, (2010), 439-450.
McBeth, John, et al., "Hypothalamic-pituitary-adrenal stress axis function and the relationship with chronic widespread pain and its antecedents", [Online]. Retrieved from the Internet: <URL: http://arthritis-research.com/content/7/5/R992, (2005), R992-R1000.
McCarthy, K. F., et al., "Cerebrospinal fluid levels of glial cell-derived neurotrophic factor correlate with spinal cord stimulation frequency in patients with neuropathic pain: a preliminary report", Spinal Cord 52, (2014), S8-S10.
Mironer, Y. Eugene, et al., "Pain Tolerance Threshold: A Pilot Study of an Objective Measurement of Spinal Cord Stimulator Trial Results", Pain Medicine, vol. 1, No. 2, (2000), 110-115.

Moseley, G. Lorimer, et al., "Tactile Discrimination, but not tactile stimulation alone, reduces chronic limg pain", Pain 137, (2008), 600-608.
Mylius, Vett, et al., "Sex differences in nociceptive withdrawal reflex and pain perception", Somatosensory and Motor Research 22 (3), (Sep. 2005), 207-211.
Neblett, Randy, et al., "What Is The Best Surface EMG Measure of Lumbar Flexion-Relation for Distinguishing Chronic Low Back Pain Patients From Pain-Free Controls?", Clin J Pain 29 (4)—NIH Public Access, (Apr. 2013), 334-340.
Palermo, Tonya M., et al., "Subjective Sleep Disturbances in Adolescents With Chronic Pain: Relationship to Daily Functioning and Quality of Life", The Journal of Pain, vol. 6, No. 3, (Mar. 2995), 201-207.
Panjabi, Manohar, "Clinical spinal instability and low back pain", Journal of Electromyography and Kinesiology 13, (2003), 371-379.
Patti, Gary J., et al., "Metabolomics implicates altered sphingolipids in chronic pain of neuropathic origin", nature chemical biology, vol. 8, (Mar. 2012), 232-234.
Plaza-Manzano, Gustavo, et al., "Changes in Biochemical Markers of Pain Perception and Stress Response After Spinal Manipulation", Journal of Orthopaedic & Sports Physical Therapy, vol. 44, No. 4, (Apr. 2014), 231-239.
Pleger, Burkhard, et al., "Patterns of cortical reorginization parallel impaired tactile discrimination and pain intensity in complex regional pain syndrome", NeuroImage 32, (2006), 503-510.
Pluijms, Wouter A., et al., "Increased Contact Heat Evoked Potential Stimulation Latencies in Responders to Spinal Cord Stimulation for Painful Diabetic Cord Stimulation for Painful Diabetic Cord Stimulation for Painful Diabetic Polyneuropathy", Neuromodulation 18, (2015), 126-132.
Prichep, Leslie S., et al., "Evaluation of the Pain Matrix Using EEG Source Localization: A Feasibility Study", Pain Medicine 12, (2011), 1241-1248.
Raminen, Tina, et al., "The Impact of Spinal Cord Stimulation on Sleep Patterns", Neuromodulation 19, (2016), 477-481.
Rasche, Dirk, et al., "Quantitative Sensory Testing in Patients With Chronic Unilateral Radicular Neuropathic Pain and Active Spinal Cord Stimulation", Neuromodulation, vol. 9, No. 3, (2006), 239-247.
Rhudy, Jamie L., et al., "Defining the nociceptive flexion reflex (NFR) threshold in human participants: A comparison of different scoring criteria", Pain 128, (2007), 244-253.
Sacco, Marcella, et al., "The Relationship Between Blood Pressure and Pain", The Journal of Clinical Hypertension vol. 15, No. 8, (Aug. 2013), 600-605.
Sarnthein, Johannes, et al., "Increased EEG power and slowed dominant frequncy in patients with neurogenic pain", Brain 129, (2005), 55-64.
Sato, Karina L/, et al., "Spinal Cord Stimulation (SCS) Improves Decreased Physical Activity Induced by Nerve Injury", Behavioral Neuroscience, vol. 128, No. 5, (2914), 625-632.
Sawada, Yukihiro, et al., "Normalized pulse volume (NPV) derived photo-plethysmography as a more valid measure of the finger vascular tone", International Journal of Psychophysiology 41, (2001), 1-10.
Sayar, Kemal, et al., "Sleep Quality in Chronic Pain Patients", Can J. Psychiatry, vol. 47, No. 9, (Nov. 2002), 844-848.
Schulman, Joshua J., et al., "Thalamocortical dysrhythmia syndrome: MEG imaging of neuropathic pain", (Jul. 25, 2014), 33-39.
Schulz, Enrico, et al., "Prefrontal Gamma Oscillations Encode Tonic Pain in Humans", Cerebral Cortex 2015, (Mar. 8, 2015), 1-8.
Sesay, Musa, et al., "Responses of Heart Rate Variability to Acute Pain After Minor Spinal Surgery: Optimal Thresholds and Correlation With the Numeric Rating Scale", J Neurosurg Anesthesiol, vol. 00, No. 00, (2014), 1-7.
Siddall, Phillip J., et al., "Magnetic Resonance Spectroscopy Detects Biochemical Changes in the Brain Associated with Chronic Low Back Pain: A Preliminary Report", Anesth Analg 102, (2006), 1164-1168.
Simoes, Mario A., "Feasibility of Wearable Sensors to Determine Gait Parameters", University of South Florida Scholar Commons, (2011), 1-98.

(56) References Cited

OTHER PUBLICATIONS

Skljarevski, V., et al., "The nociceptive flexion reflex in humans—review article", Pain, 96, (2002), 3-8.

Smallwood, Rachel F., et al., "Structural Brain Anomalies and Chronic Pain: A Quantitative Meta-Analysis of Gray Matter Volume", The Journal of Pain, vol. 14, No. 7, (Jul. 2013), 663-675.

Staud, Roland, "Heart rate variability as a biomarker of fibromyalgia syndrome", Fut Rheumatol 3 (5)—NIH Public Access, (Oct. 1, 2008), 475-483.

Storm, H., et al., "Skin conductance correlates with perioperative stress", Acta Anaesthesiol Scand 46, (2002), 887-895.

Sturgeon, John A., et al., "Respiratory Sinus Arrhythmia: a Marker of Resilience to Pain Induction", Int.J. Behav. Med. 21, (2014), 961-965.

Swenne, C. A., "Baroreflex sensitivity: mechanisms and measurement", Neth Heart J 21, (2013), 58-60.

Symons, Frank J., et al., "Can Biomarkers Differentiate Pain and No Pain Subgroups of Nonverbal Children with Cerebral Palsy? A Preliminary Investigation Based on Noninvasive Saliva Sampling", Pain Med 16 (2), (2015), 249-256.

Tagliazucchi, Enzo, et al., "Brain resting state is disrupted in chronic back pain patients", Neurosci Lett. 485 (1)—NIH Public Access, (Nov. 12, 2010), 26-31.

Tao, Weijun, et al., "Gait Analysis Using Wearable Sensors", Sensors 12, (2012), 2255-2283.

Tauda, Makoto, et al., "P2X4receptorsandneuropathicpain", Frontiers in Cellular Neuroscience, vol. 7, Article 191, (Oct. 28, 2013), 1-6.

Terkelsen, Astrid J., et al., "Heart Rate Variability in Complex Regional Pain Syndrome during Rest and Mental and Orthostatic Stress", Anesthesiology, vol. 116, No. 1, (Jan. 2012), 133-146.

Thankur, Pramodsingh Hirasingh, et al., "Method and Apparatus for Pain Management Using Heart Sounds", U.S. Appl. No. 62/395,641, filed Sep. 16, 2016.

Theuvenel, Peter J., et al., "Responses to Median and Tbial Nerve Stimulation in Patients with Chronic Neuropathic Pain", Brain Topography, vol. 11, No. 4, (1999), 306-313.

Uceyler, Nuncan, et al., "Differential expression of cytokines in painful and painless neuropathies", (2007).

Uzar, E., et al., "Serum cytokine and pro-brain natriuretic peptide (BNP) levels in patients with migraine", European Review for Medical and Pharmacological Sciences; 15, (2011), 1111-1116.

Van Velzen, Marit H.N., et al., "Effect of heat-induced pain stimuli on pulse transit time and pulse wave amplitude in healthy volunteers", Physiological Measurement 37, (2016), 52-66.

Villarejo, Viqueira Maria, et al., "A Stress Sensor Based on Galvanic Skin Response (GSR) Controlled by ZigBee", Sensors 12, (2012), 6075-6101.

Walton, K. D., et al., "Abnormal thalamocortical activity in patients with Complex Regional Pain Syndrome (CRPS) Type 1", Pain 150, (2010), 41-51.

Willer, Jean Claude, "Comparative Study of Perceived Pain and Nociceptive Flexion Reflex in Man", Pain, 3, (1977), 69-80.

Williams, Dewayne P., et al., "Effects of Chronic Pelvic Pain on Heart Rate Variability in Women", The Journal of Urology, vol. 194 (Nov. 2015), 1-6.

Wong, Arnold Y.L., et al., "Does experimental low back pain change posteroanterior lumbar spinal stiffness and trunk muscle activity? A randomized crossover study", Clinical Biomechanics 34, (2016), 45-52.

Wong, Jih-Sen, et al., "A comparative study of pulse rate variability and heart rate variability in healthy subjects", J Clin Monit Comput 26, (2012), 107-114.

Zamuner, Antonio R., et al., "Respiratory Sinus Arrhythmia and its Association with Pain in Women with Fibromyalgia Syndrome", Pain Practice, vol. 16, Issue 6, (2016), 704-711.

Zamunér, A. R., et al., "Relationship between sympathetic activity and pain intensity in fibromyalgia", Clin Exp Rheumatol 33—Abstract, [Online]. Retrieved from the Internet: <URL: http://www.ncbi.nlm.nih.gov.ezp3.lib.umn.edu/pubmed/25786044, (Feb. 2015), 1-2.

Zhang, John, "Effect of Chiropractic Care on Heart Rate Variability and Pain in a Multisite Clinical Study", Jimmal of Manipulative and Physiological Therapeutics, vol. 29, No. 4, (2006), 267-274.

Zhou, Jing, et al., "Recurrent Convolutional Neural Network Regression for Continuous Pain Intensity Estimation in Video", Technical Report, (May 3, 2016), 1-11.

"U.S. Appl. No. 15/687,925, Final Office Action dated Feb. 14, 2019", 10 pgs.

"U.S. Appl. No. 15/687,925, Non Final Office Action dated Jun. 11, 2019", 11 pgs.

"U.S. Appl. No. 15/687,925, Non Final Office Action dated Oct. 9, 2018", 9 pgs.

"U.S. Appl. No. 15/687,925, Response filed Jan. 9, 2019 to Non Final Office Action dated Oct. 9, 2018", 9 pgs.

"U.S. Appl. No. 15/687,925, Response filed May 13, 2019 to Final Office Action dated Feb. 14, 2019", 11 pgs.

"U.S. Appl. No. 15/688,676, Examiner Interview Summary dated Sep. 25, 2019", 3 pgs.

"U.S. Appl. No. 15/688,676, Final Office Action dated Jul. 29, 2019", 7 pgs.

"U.S. Appl. No. 15/688,676, Non Final Office Action dated Jan. 11, 2019", 7 pgs.

"U.S. Appl. No. 15/688,676, Response filed Sep. 25, 2019 to Final Office Action dated Jul. 29, 2019", 10 pgs.

"U.S. Appl. No. 15/688,676, Response filed Apr. 9, 2019 to Non Final Office Action dated Jan. 11, 2019", 12 pgs.

"U.S. Appl. No. 15/711,578, Examiner Interview Summary dated Aug. 28, 2019", 3 pgs.

"U.S. Appl. No. 15/711,578, Non Final Office Action dated May 23, 2019", 6 pgs.

"U.S. Appl. No. 15/711,578, Repsonse filed Aug. 23, 2019 to Non Final Office Action dated May 23, 2019", 11 pgs.

"U.S. Appl. No. 15/711,578, Supplemental Response filed Aug. 28, 2019 to Non Final Office Action dated May 23, 2019", 11 pgs.

"U.S. Appl. No. 15/867,756, Examiner Interview Summary dated Aug. 28, 2019", 3 pgs.

"U.S. Appl. No. 15/867,756, Non Final Office Action dated Jul. 1, 2019", 8 pgs.

"U.S. Appl. No. 15/867,756, Response filed Aug. 29, 2019 to Non Final Office Action dated Jul. 1, 2019", 11 pgs.

"U.S. Appl. No. 15/867,760, Examiner Interview Summary dated Aug. 28, 2019", 3 pgs.

"U.S. Appl. No. 15/867,760, Non Final Office Action dated Jul. 1, 2019", 8 pgs.

"U.S. Appl. No. 15/867,760, Response filed Aug. 29, 2019 to Non-Final Office Action dated Jul. 1, 2019", 11 pgs.

"U.S. Appl. No. 15/867,801, Non Final Office Action dated Sep. 30, 2019", 10 pgs.

"U.S. Appl. No. 15/888,808, Non Final Office Action dated Sep. 11, 2019", 7 pgs.

"Australian Application Serial No. 2017325823, First Examination Report dated Jun. 19, 2019", 3 pgs.

"Australian Application Serial No. 2017334841, First Examination Report dated Jun. 24, 2019", 3 pgs.

"Australian Application Serial No. 2017335497, First Examination Report dated Jun. 26, 2019", 3 pgs.

"International Application Serial No. PCT/US2017/048867, International Preliminary Report on Patentability dated Mar. 28, 2019", 8 pgs.

"International Application Serial No. PCT/US2017/048867, International Search Report dated Nov. 13, 2017", 5 pgs.

"International Application Serial No. PCT/US2017/048867, Written Opinion dated Nov. 13, 2017", 6 pgs.

"International Application Serial No. PCT/US2017/048896, International Preliminary Report on Patentability dated Apr. 11, 2019", 8 pgs.

"International Application Serial No. PCT/US2017/048896, International Search Report dated Nov. 27, 2017", 5 pgs.

"International Application Serial No. PCT/US2017/048896, Written Opinion dated Nov. 27, 2017", 6 pgs.

(56) References Cited

OTHER PUBLICATIONS

"International Application Serial No. PCT/US2017/052685, International Preliminary Report on Patentability dated Apr. 11, 2019", 6 pgs.
"International Application Serial No. PCT/US2017/052685, International Search Report dated Jan. 4, 2018", 5 pgs.
"International Application Serial No. PCT/US2017/052685, Written Opinion dated Jan. 4, 2018", 6 pgs.
"International Application Serial No. PCT/US2017/057367, International Preliminary Report on Patentability dated May 9, 2019", 6 pgs.
"International Application Serial No. PCT/US2017/057367, International Search Report dated Jan. 19, 2018", 4 pgs.
"International Application Serial No. PCT/US2017/057367, Written Opinion dated Jan. 19, 2018", 4 pgs.
"International Application Serial No. PCT/US2018/013257, International Preliminary Report on Patentability dated Jul. 25, 2019", 8 pgs.
"International Application Serial No. PCT/US2018/013257, International Search Report dated Apr. 19, 2018", 4 pgs.
"International Application Serial No. PCT/US2018/013257, Written Opinion dated Apr. 19, 2018", 6 pgs.
Ambady, Nalini, et al., "Thin Slices of Expressive Behavior as Predictors of Interpersonal Consequences: A Meta-Analysis", Psychological Bulletin, 1992, vol. 111, No. 2, 256-274.
Annoni, Elizabeth M., et al., "Pain Management Based on Brain Activity Monitoring", U.S. Appl. No. 62/445,061, filed Jan. 11, 2017.
Annoni, Elizabeth M., et al., "Pain Management Based on Muscle Tension Measurements", U.S. Appl. No. 62/445,092, filed Jan. 11, 2017.
Annoni, Elizabeth M., et al., "Pain Management Based on Respiration-Mediated Heart Rates", U.S. Appl. No. 62/445,069, filed Jan. 11, 2017.
Annoni, Elizabeth M., et al., "Patient-Specific Calibration of Pain Quantification", U.S. Appl. No. 62/445,095, filed Jan. 11, 2017.
Bansevicius, Dalius, et al., "Mental stress of long duration: EMG activity, perceived tension, fatigue, and pain development in pain-free subjects", Headache: The Journal of Head and Face Pain; 37.8, (1997), 499-510.
Bartlett, Marian Stewart, et al., "Automatic Decoding of Facial Movements Reveals Deceptive Pain Expressions", Current Biology 24, 738-743, Mar. 31, 2014.
Berthomier, Christian, et al., "Automatic analysis of single-channel sleep EEG: validation in healthy individuals", Sleep—New York Then Westchester—30.11, (2007), 1587-1595.
Bunde, Armin, et al., "Correlated and uncorrelated regions in heart-rate fluctuations during sleep", Physical Review Letters 85.17, (2000), 3736-3739.
Chen, Shuzhen, et al., "The role of the autonomic nervous system in hypertension: a bond graph model study", Physiological measurement 29.4 (2008): 473, (2008), 473-495.
Clark, Bryan Allen, et al., "Pain Management Based on Functional Measurements", U.S. Appl. No. 62/445,075, filed Jan. 11, 2017.
Elgendi, Mohamed, "On the analysis of fingertip photoplethysmogram signals", Current cardiology reviews 8.1, (2012), 14-25.
Fagius, J., et al., "The cold pressor test: effects on sympathetic nerve activity in human muscle and skin nerve fascicles", Acta physiologica Scandinavica 137.3, (1989), 325-334.
Foo, H., et al., "Brainstem modulation of pain during sleep and waking", Sleep medicine reviews 7.2, (2003), 145-154.
Frederiks, Joost, et al., "Within-subject electrocardiographic differences at equal heart rates: role of the autonomic nervous system", Pflügers Archiv 441.5, (2001), 717-724.
Gesche, Heiko, et al., "Continuous blood pressure measurement by using the pulse transit time: comparison to a cuff-based method", European journal of applied physiology 112.1, (2012), 309-315.
Godfrey, A., et al., "Direct measurement of human movement by accelerometry", Medical Engineering & Physics 30 (2008) 1364-1386.
Godfrey, A., et al., "Instrumenting gait with an accelerometer: a system and algorithm examination", Medical Engineering & Physics, Mar. 2015, doi:10.1016/j.medengphy.2015.02.003, 24 pgs.
Jensen, MP, et al., "Brain EEG activity correlates of chronic pain in persons with spinal cord injury: clinical implications", Nature; Spinal Cord; 51, (Jul. 17, 2012), 55-58.
Littlewort, Gwen C., et al., "Automatic Coding of Facial Expressions Displayed During Posed and Genuine Pain", Image and Vision Computing, 27(12) p. 1741-1844.
Looney, David, et al., "The In-the-Ear Recording Concept", IEEE Pulse Nov./Dec. 2012, 32-42.
McCracken, Lance M., et al., "Disrupted sleep patterns and daily functioning in patients with chronic pain", Pain Res Manage vol. 7 No. 2 Summer 2002 75-79.
Mikkelsen, Kaare B., et al., "EEGRecordedfromtheEar:CharacterizingtheEar-EEGMethod", FrontiersinNeuroscience|www.frontiersin.org, Nov. 2015|vol. 9|Article438, 8 pgs.
Moxham, I.M., "Understanding Arterial Pressure Waveforms", Southern African Journal of Anaesthesia and Analgesia 9.1, (2003), 40-42.
Mukkamala, R., et al., "Toward ubiquitous blood pressure monitoring via pulse transit time: theory and practice", IEEE Transactions on Biomedical Engineering 62.8, (2015), 1879-1901.
Ng, Joseph, et al., "EMG activity of trunk muscles and torque output during isometric axial rotation exertion: a comparison between back pain patients and matched controls", Journal of Orthopaedic Research; 20, (2002), 112-121.
Perruchoud, Christophe, et al., "Assessment of Physical Activity of Patients with Chronic Pain", Neuromodulation: Technology at the Neural Interface; 17, (2012), 42-47.
Pinheiro, Eulália Silva Dos Santos, et al., "Electroencephalographic Patterns in Chronic Pain: A Systematic Review of the Literature", PLOS ONE |DOI:10.1371/journal.pone.0149085 Feb. 25, 2016, 27 pgs.
Poon, C.C.Y., "Cuff-less and noninvasive measurements of arterial blood pressure by pulse transit time", 2005 IEEE Engineering in Medicine and Biology 27th Annual Conference. IEEE, 2006., (2006), 5877-5880.
Prkachin, Kenneth, "The consistency of facial expressions of pain: a comparison across modalities", PAIN, 51, (1992), 279-306.
Roy, Sourav Dey, et al., "An Approach for Automatic Pain Detection through Facial Expression", Procedia Computer Science 84 (2016) 99-106.
Sano, Akane, et al., "Quantitative analysis of wrist electrodermal activity during sleep", Int J Psychophysiol. Dec. 2014; 94(3), (2014), 382-389.
Shouldice, R., "PR and PP ECG intervals as indicators of autonomic nervous innervation of the cardiac sinoatrial and atrioventricular nodes", Neural Engineering, 2003. Conference Proceedings. First International IEEE EMBS Conference on. IEEE, (Mar. 2003), 261-264.
Sihvonen, T., et al., "Electric behavior of low back muscles during lumbar pelvic rhythm in low back pain patients and healthy controls", Archives of physical medicine and rehabilitation; 72.13, (1991), 1080-1087.
Srivastava, Kyle Harish, et al., "Pain Management Based on Cardiovascular Parameters", U.S. Appl. No. 62/445,053, filed Jan. 11, 2017.
Srivastava, Kyle Harish, et al., "Pain Management Based on Emotional Expression Measurements", U.S. Appl. No. 62/445,082, filed Jan. 11, 2017.
Thakur, Pramodsingh Hirasingh, et al., "Method and Apparatus for Pain Control Using Baroreflex Sensitivity During Posture Change", U.S. Appl. No. 62/412,587, filed Oct. 25, 2016.
Thakur, Pramodsingh Hirasingh, et al., "Systems and Methods for Closed-Loop Pain Management", U.S. Appl. No. 62/400,313, filed Sep. 27, 2016.
Wu, Hao-Yu, et al., "Eulerian Video Magnification for Revealing Subtle Changes in the World", ACM Transactions on Graphics 31(4), (2012), 1-8.

(56) References Cited

OTHER PUBLICATIONS

Zeng, Zhihong, et al., "A Survey of Affect Recognition Methods: Audio, Visual and Spontaneous Expressions", ICMI'07, Nov. 12-15, 2007, 126-133.
Zhou, Jing, et al., "Recurrent Convolutional Neural Network Regression for Continuous Pain Intensity Estimation in Video", arXiv preprint arXiv:1605.00894 (2016) 84-92.

* cited by examiner

METHOD AND APPARATUS FOR PAIN CONTROL USING BAROREFLEX SENSITIVITY DURING POSTURE CHANGE

CLAIM OF PRIORITY

This application claims the benefit of priority under 35 U.S.C. § 119(e) of U.S. Provisional Patent Application Ser. No. 62/412,587, filed on Oct. 25, 2016, and U.S. Provisional Patent Application Ser. No. 62/451,455, filed on Jan. 27, 2017, each of which is herein incorporated by reference in its entirety.

TECHNICAL FIELD

This document relates generally to medical devices and more particularly to a pain management system that produces a measure of pain using baroreflex sensitivity.

BACKGROUND

Pain may result from an injury, a disease (e.g., arthritis, fibromyalgia), or even a medical treatment (e.g., certain cancer treatment). Various treatments are applied for pain management, such as medication, psychotherapy, electrical stimulation, thermal therapy, and their various combinations. Examples of electrical stimulation for pain management include Transcutaneous Electrical Nerve Stimulation (TENS) delivered by a TENS unit and Spinal Cord Stimulation (SCS) that may be delivered by an implantable neuromodulation systems. Pain treatment may be prescribed based on an assessment of a patient's symptoms and underlying conditioning and titrated based on the patient's response to the treatment. As pain is not directly measurable by a machine, the assessment of the condition and the titration of the therapy may depend on questioning and/or visually assessing the patient.

SUMMARY

An Example (e.g., "Example 1") of a system for providing a patient with pain management includes a pain monitoring circuit. The pain monitoring circuit may include parameter analyzer circuitry and pain score generator circuitry. The parameter analyzer circuitry may be configured to receive and analyze one or more timing parameters and one or more baroreflex parameters allowing for determination of baroreflex sensitivity (BRS) of the patient. The one or more timing parameters are indicative of time intervals during which values of the one or more baroreflex parameters are used to determine the BRS. The pain score generator circuitry may be configured to compute a pain score using an outcome of the analysis. The pain score is a function of the BRS during the time intervals and indicative of a degree of pain of the patient.

In Example 2, the subject matter of Example 1 may optionally be configured to further include a pain relief device configured to deliver one or more pain-relief therapies to the patient and a control circuit configured to control the delivery of the one or more pain-relief therapies using the computed pain score.

In Example 3, the subject matter of any one or any combination of Examples 1 and 2 may optionally be configured such that the parameter analyzer circuitry is further configured to generate a BRS signal metric using the one or more timing parameters and the one or more baroreflex parameters, and the pain score generator circuitry is further configured to compute the pain score using the BRS signal metric.

In Example 4, the subject matter of Example 3 may optionally be configured such that the parameter analyzer circuitry is further configured to generate the BRS signal metric using the one or more timing parameters, the one or more baroreflex parameters, and at least one parameter selected from a physiological parameter indicative of a physiological function or state of the patient, a functional parameter indicative of a physical activity or state of the patient, or a patient parameter including subjective information provided by the patient.

In Example 5, the subject matter of any one or any combination of Examples 1 to 4 may optionally be configured such that the parameter analyzer circuitry is further configured to receive and analyze one or more posture parameters of the one or more timing parameters and the one or more baroreflex parameter, the one or more posture parameters indicative of a posture of the patient, and is further configured to determine the spontaneous BRS of the patient as a function of the level of physical activity of the patient.

In Example 6, the subject matter of Example 5 may optionally be configured such that the one or more posture parameters include a parameter indicative of one or more of a type, a magnitude, a duration, a velocity, or an acceleration of a change in the posture of the patient, and the parameter analyzer circuitry is configured to generate the BRS signal metric representative of the BRS of the patient being a function of the one or more of the type, the magnitude, the duration, the velocity, or the acceleration of the change in the posture of the patient.

In Example 7, the subject matter of any one or any combination of Examples 1 to 6 may optionally be configured such that the parameter analyzer circuitry is further configured to receive and analyze one or more activity parameters of the one or more timing parameters and the one or more baroreflex parameter and is further configured to determine the spontaneous BRS of the patient as a function of the level of physical activity of the patient. The one or more activity parameters are indicative of a level of physical activity of the patient, In Example 8, the subject matter of any one or any combination of Examples 1 to 7 may optionally be configured such that the parameter analyzer circuitry is further configured to receive and analyze one or more respiratory parameters of the one or more timing parameters and the one or more baroreflex parameter, and is further configured to determine the spontaneous BRS of the patient using values of the one or more baroreflex parameters during one or more of inspiration phases or expiration phases of the respiratory cycles of the patient. The one or more respiratory parameters are indicative of respiratory cycles of the patient. The respiratory cycles each include an inspiration phase and an expiration phase.

In Example 9, the subject matter of any one or any combination of Examples 5 to 8 may optionally be configured such that the pain monitoring circuit further includes one or more baroreflex sensors configured to sense one or more baroreflex signals allowing for the determination of the spontaneous BRS, a baroreflex sensing circuit configured to process the sensed one or more baroreflex signals, and a baroreflex feature detector configured to detect one or more baroreflex signal features using the processed one or more baroreflex signals, and the parameter generator is further configured to generate the one or more baroreflex parameters using the detected one or more baroreflex signal features.

In Example 10, the subject matter of Example 9 may optionally be configured such that the parameter generator is further configured to generate a heart rate or a change of the heart rate of the one or more baroreflex parameters.

In Example 11, the subject matter of any one or any combination of Examples 9 and 10 may optionally be configured such that the baroreflex parameter generator is further configured to generate a blood pressure or a change of the blood pressure of the one or more baroreflex parameters. The blood pressure is an actual blood pressure of the patient or a surrogate of the blood pressure of the patient.

In Example 12, the subject matter of Example 11 may optionally be configured such that the baroreflex parameter generator is further configured to generate an amplitude of second heart sounds (S2) or a pulse transit time (PTT) as the surrogate of the blood pressure of the patient.

In Example 13, the subject matter of any one or any combination of Examples 9 to 12 may optionally be configured such that the baroreflex parameter generator is further configured to generate a heart sound parameter of the one or more baroreflex parameters. The heart sound parameter is representative of an amplitude of a heart sound or a time interval associated with the heart sound.

In Example 14, the subject matter of any one or any combination of Examples 9 to 13 may optionally be configured such that the baroreflex parameter generator is further configured to generate a heart rate variability parameter of the one or more baroreflex parameters. The heart rate variability parameter is a measure of heart rate variability of the patient.

In Example 15, the subject matter of any one or any combination of Examples 9 to 14 may optionally be configured such that the baroreflex parameter generator is further configured to generate a neural parameter of the one or more baroreflex parameters. The neural parameter is indicative of neural activities associated relaying information about blood pressure of the patient.

An example (e.g., "Example 16") of a method for managing pain of a patient is also provided. The method may include receiving and analyzing one or more timing parameters and one or more baroreflex parameters allowing for determination of baroreflex sensitivity (BRS) of the patient. The one or more timing parameters are indicative of time intervals during which values of the one or more baroreflex parameters are used to determine the BRS. The method may further include computing a pain score using an outcome of the analysis, the pain score being a function of the BRS during the time intervals and indicative of a degree of pain of the patient.

In Example 17, the subject matter of Example 16 may optionally further include: delivering one or more pain-relief therapies to the patient from a pain relief device, and controlling the delivery of the one or more pain-relief therapies using the pain score.

In Example 18, the subject matter of analyzing the one or more timing parameters and the one or more baroreflex parameters as found in any one or any combination of Examples 16 and 17 may optionally further include: generating a BRS signal metric using the one or more timing parameters and the one or more baroreflex parameters, and the subject matter of computing the pain score as found in any one or any combination of Examples 16 and 17 may optionally further include computing the pain score using the BRS signal metric.

In Example 19, the subject matter of any one or any combination of Examples 16 to 18 may optionally further include: sensing one or more posture signals indicative of a posture of the patient using one or more activity sensors, and generating one or more posture parameters of the one or more timing parameters using the one or more posture signals.

In Example 20, the subject matter of any one or any combination of Examples 16 to 19 may optionally further include: sensing one or more activity signals indicative of a level of physical activity of the patient using one or more activity sensors, and generating one or more activity parameters of the one or more timing parameters using the one or more activity signals.

In Example 21, the subject matter of any one or any combination of Examples 16 to 20 may optionally further include: sensing one or more respiratory signals indicative of respiratory cycles of the patient using one or more respiratory sensors, and generating one or more respiratory parameters of the one or more timing parameters using the one or more respiratory signals.

In Example 22, the subject matter of any one or any combination of Examples 16 to 21 may optionally further include: sensing one or more baroreflex signals allowing for the determination of the BRS using one or more baroreflex sensors, and generating the one or more baroreflex parameters using the one or more baroreflex signals.

In Example 23, the subject matter of sensing the one or more baroreflex signals as found in Example 22 may optionally further include sensing one or more of a cardiac signal indicative of a heart rate of the patient or a blood pressure signal indicative of a blood pressure of the patient.

In Example 24, the subject matter of generating the one or more baroreflex parameters as found in Example 23 may optionally further include generating a parameter indicative of one or more of a heart rate, a change in the heart rate, a slope of change in the heart rate, or a heart rate variability.

In Example 25, the subject matter of generating the one or more baroreflex parameters as found in Example 23 may optionally further include generating a blood pressure parameter, a change in the blood pressure parameter, a slope of the change in the blood pressure parameter, or a measure of a neural activity driven by the blood pressure or the change in the blood pressure, the blood pressure parameter indicative of the blood pressure of the patient.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1A:
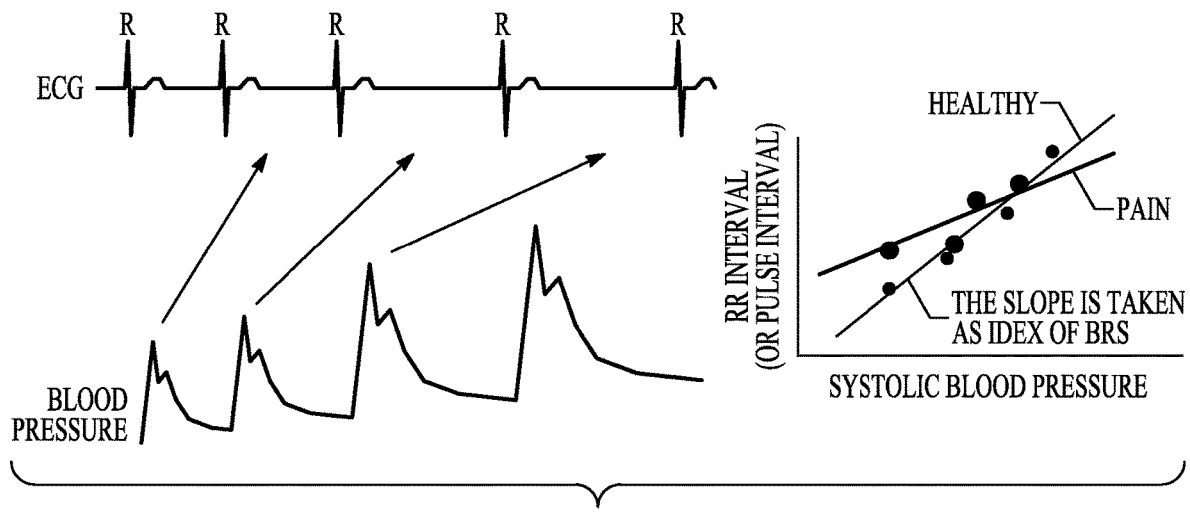
FIG. 1A illustrates an example of baroreflex sensitivity (BRS) in pain and healthy states.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses a method and system for indicating pain that can be used in a closed-loop pain management system. Because different patients may have different sensitivity and tolerance to pain, optimization of a pain relief therapy may be difficult and/or inefficient when being dependent on patent questioning and manual programming. The present system provides for an objective and quantitative measure of pain that can be used in an automated closed-loop pain management system, such as a neurostimulation or drug therapy system, to optimize pain relief. Other uses of the objective and quantitative measure of pain include, but are not limited to, improving assessments of pain relief therapies and improving patient selection for pain relief therapies. In various embodiments, the objective and quantitative measure of pain, such as in the form of a pain score, can be used as a stand-alone indicator for monitoring pain in a patient in a hospital or other point of care or at home, or can be used as an input for therapy optimization. For the therapy optimization, the objective and quantitative measure of pain can be used to set, adjust, and/or optimize therapy parameters based on efficacy, manually by a user and/or automatically in a closed-loop therapeutic device system. For example, in a system including a neurostimulator delivering spinal cord stimulation (SCS) for treating chronic pain, the pain score can be used during SCS trial session to optimize stimulation parameters and determine efficacy, during programming of the neurostimulator (e.g., a permanent SCS implant) to optimize pain relief, and during long-term or permanent use of the neurostimulator (e.g., the permanent SCS implant) for closed-loop control using continuous or intermittent pain assessment to optimize therapeutic stimulation parameters.

Arterial baroreflex (also referred to as baroreceptor reflex) is important for hemodynamic stability and for cardioprotection and is a strong prognostic indicator. The baroreflex regulates blood pressure (BP) via controlling heart rate, contractility, and peripheral resistance. The carotid and aortic baroreceptors detect changes in pressure, providing negative feedback to a closed-loop system for regulating blood pressure. In a healthy person, when baroreceptor activation increases due to a blood pressure increase, efferent parasympathetic activity increases to lower blood pressure through slowing the heart rate and causing peripheral vasodilation. An elevated blood pressure increases baroreflex activation, which causes the heart rate to decrease. The decreased heart rate in turn causes blood pressure to decrease. A low blood pressure decreases baroreflex activation, which causes heart rate to increase. The increased heart rate in turn causes blood pressure to increase. The baroreflex can be assessed via baroreflex sensitivity (also referred to as baroreceptor reflex sensitivity or BRS), which is a measure of how baroreflex influence the heart rate and can be calculated as the ratio of change in interbeat interval (IBI) to change in blood pressure (e.g., in ms/mmHg). BRS provides an indication of the function of this closed-loop system for regulating blood pressure and can be measured using various heart rate and blood pressure monitoring techniques.

Studies have shown that pain or other stressors can alter BRS. FIG. 1A illustrates an example of BRS in pain and healthy states. With abnormal autonomic activity associated with pain, the change in heart rate in response to change in blood pressure is attenuated, resulting in decreased BRS. One study demonstrated that psychological and physical stressors caused significant decreases in BRS, which served as a robust measure for discriminating these events from periods at rest. In a study comparing healthy people to chronic back pain patients, results indicate that patients in pain have diminished BRS. This attenuation in BRS leads to impaired sympathetic inhibition, elevated blood pressure, and amplification of persistent pain.

The present system can characterize baroreflex for use as an objective measure for pain in medical devices such as a wearable or implantable pulse generator for spinal cord stimulation, a drug pump for controlling chronic pain, or a diagnostic and/or monitoring device. In various embodiments, this objective measure for pain can be used to optimize therapy over the course of hours, weeks, or months as part of a closed-loop therapy system and/or to provide an improved measure of patient status (e.g., indicating relative changes from a pre-therapy baseline).

Figure 2:
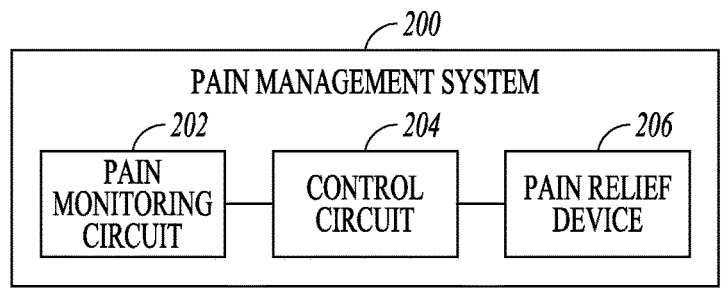
FIG. 2 illustrates an embodiment of a pain management system.

FIG. 2 illustrates an embodiment of a pain management system 200. System 200 includes a pain monitoring circuit 202, a control circuit 204, and a pain relief device 206. In various embodiments, system 200 can provide a patient with closed loop pain management in which delivery of one or more pain relief therapies can be controlled automatically using signals sensed from the patient. In various other embodiments, pain monitoring circuit 202 can be used as part of a diagnostic and/or monitoring system that does not necessarily include control circuit 204 and pain relief device 206 or other therapeutic components.

Pain monitoring circuit 202 can sense one or more signals allowing for determination of the patient's BRS, and can produce one or more pain indicating signals using the one or more sensed signals. Pain relief device 206 can deliver one or more pain relief therapies, such as any one or any combination of spinal cord stimulation (SCS), dorsal root ganglia (DRG) stimulation, deep brain stimulation (DBS), motor cortex stimulation (MCS), transcranial direct current stimulation (tDCS), transcutaneous spinal direct current stimulation (tsDCS), transcranial alternating current stimulation (tACS), trigeminal nerve stimulation, occipital nerve stimulation, vagus nerve stimulation, sacral nerve stimulation, sphenopalatine ganglion stimulation, sympathetic chain modulation, multifidus muscle stimulation, adrenal gland modulation, carotid baroreceptor stimulation, transcutaneous electrical nerve stimulation (TENS), tibial nerve stimulation, transcranial magnetic stimulation (TMS), repeated transcranial magnetic stimulation (rTMS), radiofrequency ablation (RFA), pulsed radiofrequency ablation, other peripheral tissue stimulation therapies, and drug therapy (such as delivered from a drug pump). Various neuromodulation (also referred to as neurostimulation) therapies can use any form of stimulation energy or agent as stimuli that is capable of modulating neural activities and/or properties.

Control circuit 204 can analyze the one or more physiological signals to assess the patient's BRS, and can control the delivery of the one or more pain relief therapies using an outcome of the analysis. For example, the outcome of the analysis can include a pain score indicative of a degree (intensity) of pain, and control circuit 204 controls the delivery of the one or more pain relief therapies using the pain score and one or more thresholds. Other factors affecting the degree of pain and/or effectiveness of the one or more pain relief therapies can also be included in the analysis. For example, signals other than those used in determining the patient's BRS can also be sensed, and/or patient information such as those from the patient's medical records and the patient's perception of pain, can be used in producing the pain score. The patient information can include chronic pain assessment at follow-up visits by the patient at a clinic and/or real-time indication of acute change in perception of pain based on input from the patient or inferred by patient adjusting the delivery of the one or more pain relief therapies. In various embodiments, system 200 is a closed-loop system with feedback control using the outcome of the analysis (e.g., the pain score) as an input.

In various embodiments, circuits of system 200, including various embodiments of its components discussed in this document, may be implemented using a combination of hardware and software. For example, pain monitoring circuit 202, including its various embodiments discussed in this document, and control circuit 204 may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 3:
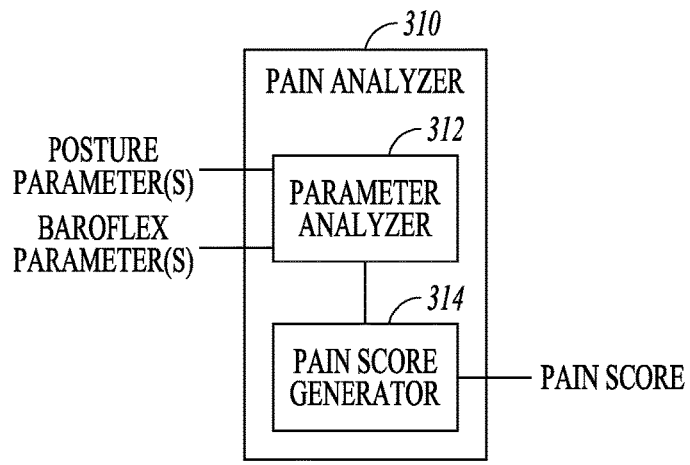
FIG. 3 illustrates an embodiment of a pain analyzer, such as may be used in the pain management system of FIG. 2.

FIG. 3 illustrates an embodiment of a pain analyzer 310. In various embodiments, pain analyzer 310 can be implemented as pain analyzer circuitry being part of the pain monitoring circuit 202. Pain analyzer 310 can include a parameter analyzer 312 and a pain score generator 314. In various embodiments, parameter analyzer 312 can be implemented as parameter analyzer circuitry configured to receive and analyze one or more timing parameters and one or more baroreflex parameters. The one or more baroreflex parameters allow for determination of BRS of the patient. The one or more timing parameters are indicative of time intervals during which values of the one or more baroreflex parameters are used to determine the BRS. The time intervals correspond to a physical and/or physiological state of the patient suitable for assessing the BRS for quantifying pain of the patient. Pain score generator 314 can be implemented as pain score generator circuitry configured to compute a pain score using an outcome of the analysis. The pain score is computed as a function of the BRS and is indicative of a degree of pain of the patient.

Various embodiments of system 200 including: (1) a system for pain management using BRS during posture change (e.g., the one or more timing parameters indicate posture change), and (2) a system for pain management using ambulatory monitoring of spontaneous BRS (e.g., the one or more timing parameters indicate physical activity level and/or phase of respiratory cycle), are discussed below by way of examples, but not by way of limitations, of the present subject matter. Other embodiments can include detection of BRS change in any manner capable of producing one or more parameters that objectively and quantitatively indicate pain in a patient.

Example: Pain Management Using BRS During Posture Change

In various embodiments, an exemplary system can sense signals indicative of posture and BRS and extract one or more features from one or more of the sensed signals to characterize BRS during posture change as a quantitative measure of pain. The result can be used to control a pain management therapy, such as being used as an input in an automated closed-loop pain relief therapy system. Examples of other applications of the result include diagnosis for pain or related symptoms and/or conditions, use as an input to a therapy titration session for a therapy, or use as a monitor for assessing patient progress. While the pain management therapy is specifically discussed as an example, the pain monitoring according to the present subject matter can be used in any application requiring monitoring of pain or related symptoms in a patient to provide a quantitative measure of the pain.

Acute pain in healthy subjects activates the sympathetic nervous system, which causes an increase in blood pressure and heart rate. The increased blood pressure in turn activates baroreceptors which down-regulate sympathetic outflow, restoring homeostasis. In healthy subjects who transition abruptly from a supine to standing position, pooling of blood in the lower extremities causes an immediate arterial blood pressure reduction, which in turn activates baroreceptors which increase sympathetic outflow causing a blood pressure and heart rate increase, again restoring homeostasis. These are healthy compensatory responses.

Figure 1B:
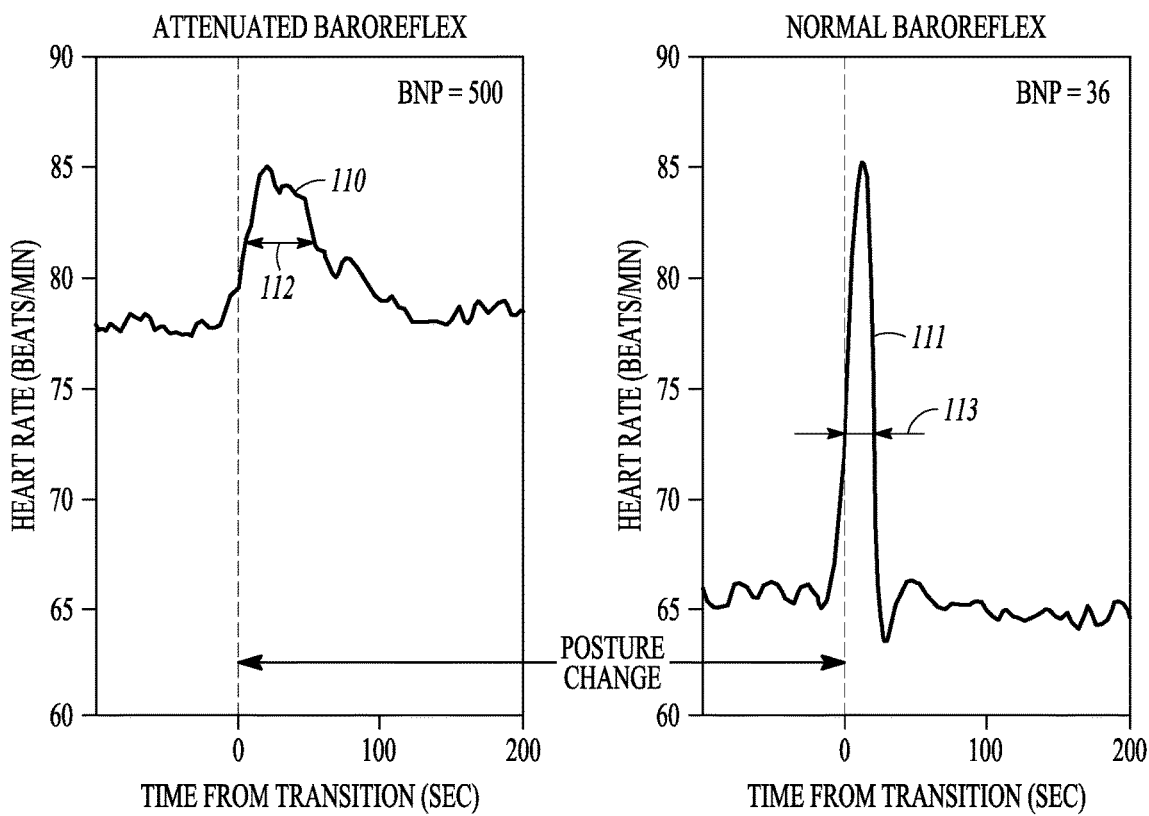
FIG. 1B illustrates an example of attenuated heart rate response due to a posture change from laying to standing.

Persistent pain tends to become chronic, however, resulting in chronically-elevated blood pressure and heart rate levels and an attenuated baroreceptor response. FIG. 1B illustrates an example of attenuated heart rate response due to a posture change from laying to standing. Such attenuated baroreceptor response can cause a reduced and delayed heart rate and blood pressure response (not shown) to a posture change (or, in response to any activity which would typically activate the baroreceptors). The "attenuated baroreflex" graph in FIG. 1 shows (a) the increased heart rate at baseline which could be expected with chronically-elevated sympathetic tone, (b) the delayed onset response and delayed recovery of the heart rate after posture change (i.e., a "fat and wide" curve), and (c) the reduced magnitude of the heart rate response when compared to the "normal baroreflex" image.

Impaired baroreflex function is also associated with severe conditions such as recurrent syncope, orthostatic hypotension, and volatile hypertension. Thus, not only does this baroreflex offer a potential biomarker of pain severity and/or chronicity, but it also offers a very valuable measure of patient health status. Improving the baroreflex sensitivity, if impaired, would be a positive therapy outcome.

Referring to FIG. 3, in various embodiments using BRS during postural change for pain management, the one or more timing signals include one or more posture parameters. Parameter analyzer 312 can receive and analyze the one or more posture parameters and the one or more baroreflex parameters. In various embodiments, the one or more posture parameters can include one or more of a posture parameter indicative of the type of the change in the posture, a posture parameter indicative of the magnitude of the change in the posture, a posture parameter indicative of the duration of the change in the posture, a posture parameter indicative of the velocity of the change in the posture, or a posture parameter indicative of the acceleration of the change in the posture. The one or more baroreflex parameters can include any one or more signals indicative of the patient's baroreflex and allow for determination of the BRS. Pain score generator 314 can compute a pain score using an outcome of the analysis. The pain score indicating of a degree (intensity) of the pain. In one embodiment, parameter analyzer 312 detects values of each baroreflex parameter of the one or more baroreflex parameter during changes in the posture, and stratifies the values of the baroreflex parameter by values of each of the one or more posture parameters.

In one embodiment, parameter analyzer 312 produces a signal metric being a measure of BRS as a function of one or more posture parameters using the one or more posture parameters and the one or more baroreflex parameters, and pain score generator 314 computes the pain score using the signal metric. In one embodiment, in addition to the one or more posture parameters and the one or more baroreflex parameters, pain analyzer 310 uses one or more additional parameters to produce the signal metric for an increased reliability of the pain score. The one or more additional parameters can be selected from one or more physiological parameters each indicative of a physiological function or state of the patient, one or more functional parameters each indicative of a physical activity or state of the patient, and/or one or more patient parameters including subjective information provided by the patient. Examples of such one or more additional parameters are discussed in U.S. Provisional Patent Application Ser. No. 62/400,336, entitled "METHOD AND APPARATUS FOR PAIN MANAGEMENT USING OBJECTIVE PAIN MEASURE", filed on Sep. 27, 2016, assigned to Boston Scientific Neuromodulation Corporation, which is incorporated herein by reference in its entirety.

The signal metric can be a linear or nonlinear combination of the one or more baroreflex parameters each as a function of the one or more posture parameters. In various embodiments, parameter analyzer 312 can produce the signal metric using multiple baroreflex parameters with the weighting factors each applied to one of these baroreflex parameters. In various embodiments, parameter analyzer 312 can adjust the weighting factors through automatic learning and adaptation to the patient over time (e.g., based on stored parameters and/or outcomes of analysis, such as features extracted from the parameters). In various other embodiments, parameter analyzer 312 can allow the weighting factors to be adjusted manually. In various other embodiments, the weighting factors can be adjusted according to a calibration schedule or as needed, and the adjustment can be performed by a user such as a physician or other authorized care provider in a clinic, or initiated by the patient and performed by parameter analyzer 312 automatically at home. In various embodiments, the weighting factors can be patient-specific and dynamically changed based on the patient's conditions and/or activities.

Figure 4:
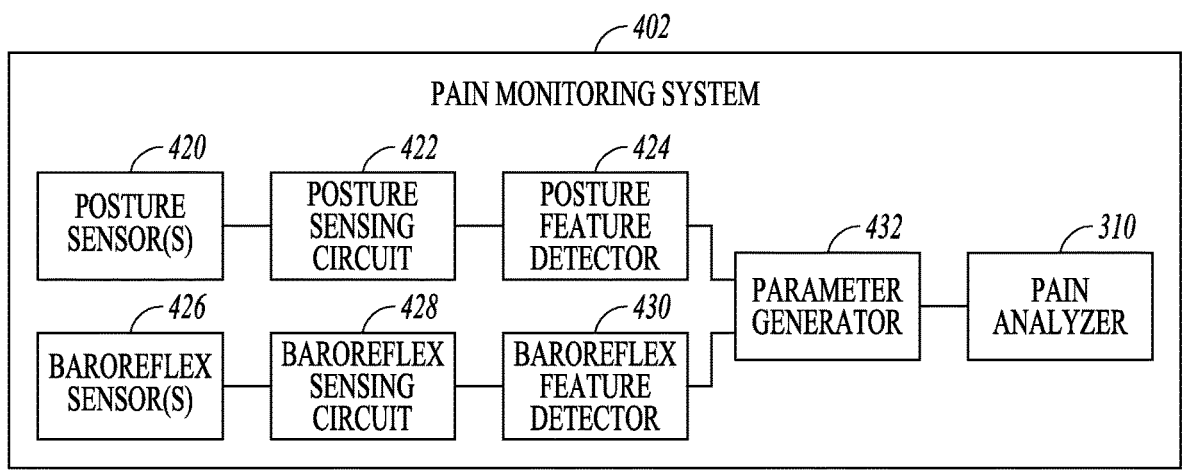
FIG. 4 illustrates an embodiment of a pain monitoring circuit, such as may be used in the pain management system of FIG. 2.

FIG. 4 illustrates an embodiment of a pain monitoring circuit 402, which represent an example of pain monitoring circuit 202. Pain monitoring circuit 402 can include one or more posture sensors 420, a posture sensing circuit 422, a posture feature detector 424, one or more baroreflex sensors 426, a baroreflex sensing circuit 428, a baroreflex feature detector 430, a parameter generator 432, and pain analyzer 310.

In various embodiments, posture sensor(s) 420 can sense one or more posture signals indicative of posture of the patient. Examples of the posture sensor(s) 420 include an accelerometer a gyroscope, a magnetometer, an impedance sensor, or any other sensor or combination of sensors capable of providing one or more sensor signals allowing for determination of one or more of type, magnitude, duration, velocity, or acceleration of the change in the patient's posture. Posture sensing circuit 422 can process the one or more posture signals. Posture feature detector 424 can detect one or more posture signal features using the processed one or more posture signals. The one or more posture signal features allow for measurement of the one or more posture parameters. Parameter generator 432 can generate one or more posture parameters using the detected one or more posture signal features. In various embodiments, the one or more posture parameters can include one or more of a posture parameter indicative of the posture of the patient, a posture parameter indicative of a change in the posture, a posture parameter indicative of a type of the change in the posture (e.g., laying to sitting, laying to standing, sitting to standing, . . . and any combinations of these types), a posture parameter indicative of a magnitude of the change in the posture (e.g., an angle of change, such as measured in degrees), a posture parameter indicative of a duration of the change in the posture (e.g., a time interval between a beginning and an ending of the change in the posture, such as measured in seconds), a posture parameter indicative of a velocity of the change in the posture (i.e., the change of the magnitude over the duration), or a posture parameter indicative of an acceleration of the change in the posture (i.e., the rate of change of the velocity).

In various embodiments, baroreflex sensor(s) 426 can sense one or more baroreflex signals each being a physiological signal allowing for determination of the BRS. Baroreflex sensing circuit 428 can process the sensed one or more baroreflex signals. Baroreflex feature detector 430 can detect one or more baroreflex signal features using the processed one or more baroreflex signals. The one or more baroreflex signal features allow for measurement of the one or more baroreflex parameters. Parameter generator 432 can generate the one or more baroreflex parameters using the detected one or more baroreflex signal features (in addition to generating the one or more posture parameters). Examples of baroreflex sensor(s) 426, the one or more baroreflex signals, and one or more baroreflex parameters are discussed below with reference to FIG. 5. In various embodiments, baroreflex sensing circuit 428 can increase the sampling and storage rates of the one or more baroreflex signals upon detection of a change in the posture by baroreflex feature detector 430 using the one or more posture parameters. Baroreflex feature detector 430 can include storage of a rolling window of the one or more baroreflex signals for use by parameter generator 432 upon detection of the change in the posture.

Figure 5:
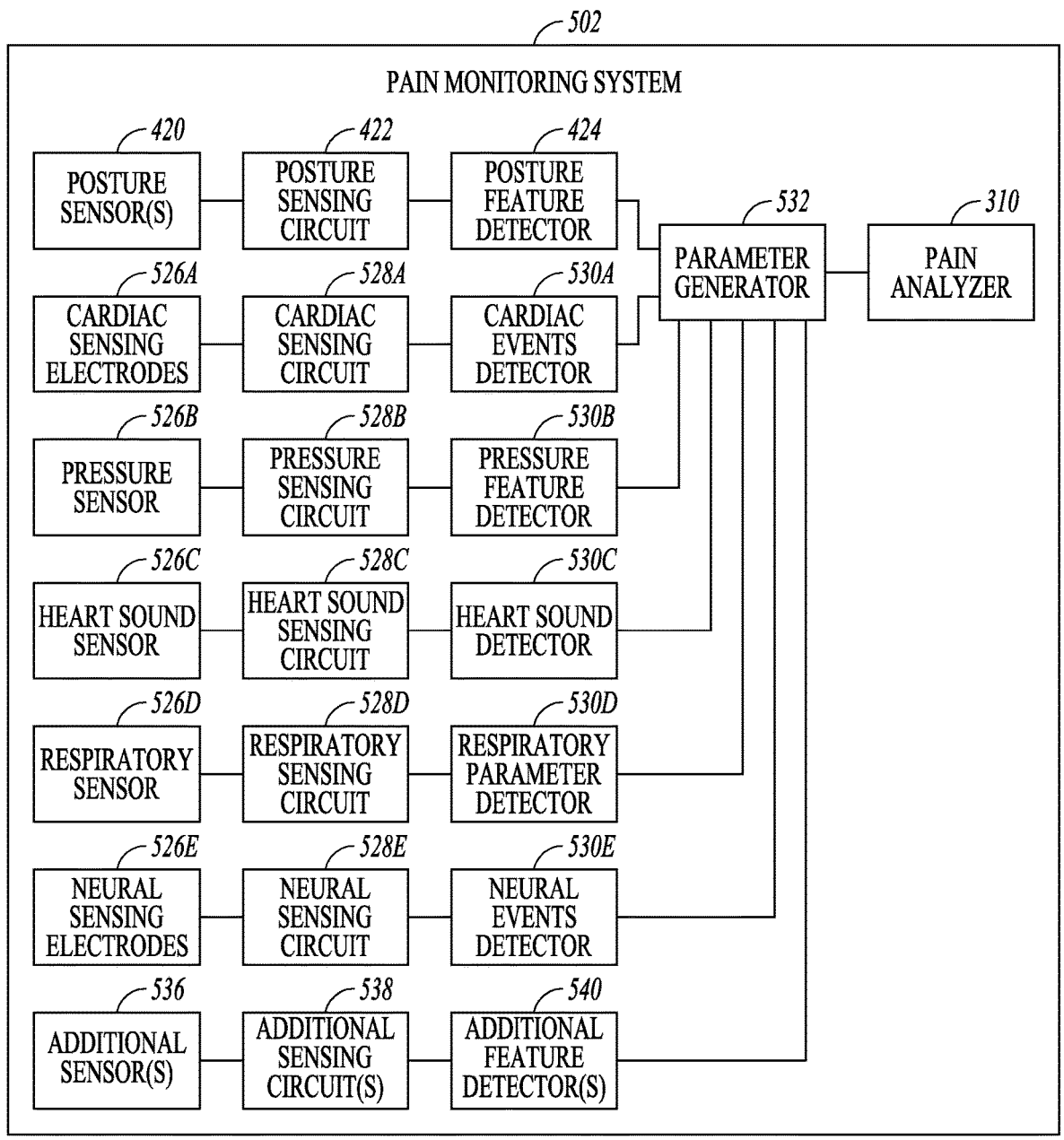
FIG. 5 illustrates another embodiment of the pain monitoring circuit, such as may be used in the pain management system of FIG. 2.

FIG. 5 illustrates an embodiment of a pain monitoring circuit 502, which represent an example of pain monitoring circuit 202 or 402. Pain monitoring circuit 502 can include posture sensor(s) 420, posture sensing circuit 422, posture feature detector 424, one or more baroreflex sensors 526, one or more baroreflex sensing circuits 528, one or more baroreflex feature detectors 530, a parameter generator 532, and pain analyzer 310. Various embodiments of baroreflex sensor(s) 526, baroreflex sensing circuit(s) 528, and baroreflex feature detector(s) 530 are shown in FIG. 5 for purposes of illustration and discussion. In various embodiments, baroreflex sensor(s) 526, baroreflex sensing circuit(s) 528, and baroreflex feature detector(s) 530 can include only those required for producing the one or more baroreflex parameters used for producing the pain score.

As illustrated in FIG. 5 and discussed below, examples of baroreflex sensor(s) 526, baroreflex sensing circuit(s) 528, and baroreflex feature detector(s) 530 include, respectively: (1) cardiac sensing electrodes 526A, a cardiac sensing circuit 528A, and a cardiac electrical events detector 530A; (2) a pressure sensor 526B, a pressure sensing circuit 528B, and a pressure feature detector 530B; (3) a heart sound sensor 526C, a heart sound sensing circuit 528C, and a heart sound detector 530C; (4) a respiratory sensor 526D, a respiratory sensing circuit 528D, and a respiratory parameter detector 530D; (5) neural sensing electrodes 526E, a neural sensing circuit 528E, and (5) a neural events detector 530E. In various embodiments, pain monitoring circuit 502 can include any one or any combination of these examples (1)-(5), depending on the one or more baroreflex parameters to be produced by parameter generator 532. In various embodiments, pain monitoring circuit 502 can optionally include one or more additional sensors 536, one or more additional sensing circuits 538, and one or more additional feature detectors 540. The additional sensor(s) 536, additional sensing circuit(s) 538, and additional feature detector(s) 540 can be used to sense additional baroreflex signal(s) and/or signal(s) not directly related to BRS but used in producing the pain score.

Cardiac sensing electrodes 526A can be used to sense one or more cardiac signals. Cardiac sensing circuit 528A can process the sensed one or more cardiac signals. Electrical event detector 530A can detect one or more cardiac electrical events (e.g., P-waves and R-waves) using the processed one or more cardiac signals. In various embodiments, the one or more cardiac signals can include surface electrocardiogram (ECG), wireless ECG (including subcutaneous ECG), and/or intracardiac electrogram. The one or more cardiac electrical events can include P-wave, Q-wave, R-wave, S-wave, and/or T-wave, depending on which one or more parameters are used for the pain analysis, as further discussed in this document. "Surface ECG" includes a cardiac electrical signal sensed with electrodes attached onto the exterior surface of the skin. "Wireless ECG" includes a signal approximating the surface ECG, acquired without using surface (non-implantable, skin contact) electrodes. "Subcutaneous ECG" is a form of wireless ECG and includes a cardiac electrical signal sensed through electrodes implanted in subcutaneous tissue, such as through electrodes incorporated onto an implantable medical device that is subcutaneously implanted. As reflected in their corresponding morphologies, the surface ECG results from electrical activities of the entire heart. The wireless ECG, including but not being limited to the subcutaneous ECG, has a morphology that approximates that of the surface ECG and reflects electrical activities of a substantial portion of the heart, up to the entire heart. Examples for sensing wireless ECG signals including subcutaneous ECG signals is discussed in U.S. Pat. No. 7,299,086, entitled "WIRELESS ECG IN IMPLANTABLE DEVICES", assigned to Cardiac Pacemakers, Inc., which is incorporated herein by reference in its entirety. One or more wireless ECG signals may be available, for example, when the patient is using an implantable pacemaker, implantable cardioverter defibrillator, or an implantable cardiac monitoring device. "Intracardiac electrogram" includes a cardiac electrical signal sensed with at least one electrode placed in or on the heart. One or more intracardiac electrographic signals may be available, for example, when the patient is using an implantable pacemaker or implantable cardioverter defibrillator. In one embodiment, cardiac sensing circuit 528A removes unwanted components of the sensed one or more cardiac signals, such as pacing artifacts when the patient uses a pacemaker.

Pressure sensor 526B can sense one or more blood pressure signals. Examples of pressure sensor 526B include blood pressure cuffs and intravascular pressure sensors. Pressure sensing circuit 528B can process the sensed one or more pressure signals. Pressure feature detector 530B can detect one or more pressure features (e.g., peaks) using the processed one or more pressure signals. In various embodiments, blood pressure is measured using a surrogate, such as the second heart sound (S2, as discussed below) or photoplethysmography (PPG, for sensing pulse transit time, as discussed below) sensor which measures blood flow with light, when direct blood pressure sensing is difficult while being unnecessary.

Heart sound sensor 526C can sense one or more heart sound signals. Examples of heart sound sensor 526C include an accelerometer or a microphone. Hearing sound sensing circuit 528C can process the one or more heart sound signals. The processing can include removal of unwanted signal components, such as patient's physical activity sensed by the accelerometer or background noise sensed by the microphone. Heart sound detector 530C can detect heart sounds using the processed one or more heart sound signals. In this document, a "heart sound signal" includes any signal indicative of heart sounds. "Heart sounds" include audible mechanical vibrations caused by cardiac activity that can be sensed with a microphone and audible and inaudible mechanical vibrations caused by cardiac activity that can be sensed with an accelerometer or optical sensor. Heart sounds include the "first heart sound" or S1, the "second heart sound" or S2, the "third heart sound" or S3, the "fourth heart sound" or S4, and their various sub-components. S1 is known to be indicative of, among other things, mitral valve closure, tricuspid valve closure, and aortic valve opening. S2 is known to be indicative of, among other things, aortic valve closure and pulmonary valve closure. S3 is known to be a ventricular diastolic filling sound often indicative of certain pathological conditions including heart failure. S4 is known to be a ventricular diastolic filling sound resulted from atrial contraction and is usually indicative of pathological conditions. The term "heart sound" hereinafter refers to any heart sound (e.g., S1) and any components thereof (e.g., M1 component of S1, indicative of Mitral valve closure). Unless noted otherwise, S1, S2, S3, and S4 refer to the first, second, third, and fourth heart sounds, respectively, as a heart sound type, or as one or more occurrences of the corresponding type heart sounds, depending on the context. In various embodiment, the heart sounds detected for producing the one or more baroreflex parameters include S1 and S2.

Respiratory sensor 526D can sense one or more respiratory signals. Respiratory sensing circuit 528D can process the sensed one or more respiratory signals. Respiratory parameter detector 530D can detect one or more respiratory parameters using the processed sensed one or more respiratory signals. The one or more respiratory signals are physiologic signals indicative of respiratory cycles (each including an inspiratory phase and expiratory phase) and various other respiratory parameters. In various embodiments, respiratory sensor 526D can sense one or more signals each directly or indirectly indicating at least the respiratory cycles. Example of respiratory sensor 526D include an acoustic sensor to sense pulmonary sounds, a flow sensor to sense airflow, a strain sensor to sense muscle strain, an impedance sensor to sense transthoracic impedance, an electrocardiographic (ECG) sensor to sense ECG (from which periods of inspiration and expiration can be derived), a heart sound sensor (as cardiac vibrations are modulated by respiratory activity), and a blood pressure sensor to sense a blood pressure (modulated by respiratory activity). In one embodiment, respiratory sensor 526D includes an impedance sensor that senses a transthoracic impedance signal indicative of respiration. In another embodiment, respiratory sensor 526D includes an implantable pulmonary artery pressure (PAP) sensor or a portion thereof. An example of the implantable PAP sensor is discussed in U.S. Pat. No. 7,566,308, entitled "METHOD AND APPARATUS FOR PULMONARY ARTERY PRESSURE SIGNAL ISOLATION", assigned to Cardiac Pacemakers, Inc., which is incorporated by reference herein in its entirety. In one embodiment, the respiratory sensor includes an external sensor that senses the expansion and contraction of the chest or a portion thereof. The processed respiratory signal (produced by respiratory sensing circuit 528D) is indicative of respiratory cycles and can allow for detection of one or more respiratory parameters such as respiratory cycle length, inspiration period, expiration period, non-breathing period, tidal volume, and minute ventilation. In one embodiment, respiratory sensing circuit 528D removes unwanted components of the sense respiratory signal to isolate the respiratory components of the physiologic signal. One example includes isolating the respiratory components of a PAP signal, which is discussed in U.S. Pat. No. 7,566,308. The one or more of the respiratory parameters detected by respiratory parameter detector 530D include any one or more parameters detectable from the processed respiratory signal and needed for producing the one or more baroreflex parameters, as further discussed in this document.

Neural sensing electrodes 526E can sense one or more neural signals. Examples of neural sensing electrodes 526E include a cuff electrode that can be placed around a nerve, or an electrode or electrode arrays that can be placed on or adjacent the nerve, to sense action potentials propagating in that nerve. Neural sensing circuit 528E can process the sensed one or more neural signals. Neural electrical event detector 530E detect one or more neural electrical events (e.g., action potentials) using the processed one or more neural signals.

Additional sensor(s) 536 can sense one or more additional signals. Examples of the one or more additional signals include one or more signals used for producing the one or more baroreflex parameters but not sensed by baroreflex sensor(s) 526 including the examples discussed above, as well as the one or more additional parameters (i.e., the one or more physiological parameters, the one or more functional parameters, and/or the one or more patient parameters, with examples discussed in U.S. Provisional Patent Application Ser. No. 62/400,336). Additional sensing circuit(s) 538 can process the one or more additional signals. Additional feature detector(s) 540 detects one or more signal features using the processed one or more additional signals. The one or more signal features allow for production of the one or more baroreflex parameters and/or the one or more additional parameters.

Parameter generator 532 can generate the one or more baroreflex parameters each being a measure of the BRS using the one or more signal features detected by baroreflex feature detector(s) 530. In some embodiments, parameter generator 532 can further generate the one or more additional parameters.

In various embodiments, the one or more baroreflex parameters generated by parameter generator 532 can include, but are not limited to, any one or any combination of examples (1)-(9) below:

(1) Heart rate, or inter-beat interval (IBI). The relationship between the heart rate and the IBI (also referred to as cardiac cycle length), as used in this document, is the relationship between a frequency and its corresponding period. If the heart rate is given in beats per minute (bpm), its corresponding IBI in milliseconds is calculated by dividing 60,000 by the heart rate (where 60,000 is the number of milliseconds in a minute). Any process using the heart rate can be modified accordingly when the IBI is used instead. Examples of the heart rate include atrial rate and ventricular rate. Examples of the IBI include atrial cycle length (interval between adjacent P-waves, i.e., P-P interval) and ventricular cycle length (interval between adjacent R-waves, i.e., R-R interval). In various embodiments, parameter generator 532 can generate the heart rate and/or IBI using the one or more cardiac signals sensed and processed by cardiac sensing electrodes 526A, cardiac sensing circuit 528A, and cardiac events detector 530A.

(2) Blood pressure. When sensing blood pressure directly is difficult, surrogates for blood pressure can be used, such as:
 a) Amplitude of the second heart sounds (S2); or
 b) Pulse transit time (PTT), which is the time interval during which a pulse pressure waveform travels between two arterial sites, such as measured from signals sensed using a photoplethysmograph (PPG) sensor that senses blood flow with light.

In various embodiments, parameter generator 532 can generate the blood pressure (or its surrogates) using the one or more pressure signals sensed and processed by pressure sensor 526B, pressure sensing circuit 528B, and pressure feature detector 530B and/or the one or more heart sound signals sensed and processed by heart sound sensor 526C, heart sound sensing circuit 528C, and heart sound detector 530C.

(3) Amplitude of the first heart sound (S1, as a measure of heart contractility) and cardiac time intervals such as:
   a) Pre-ejection period (PEP), measured as the time interval between a Q or R-wave and the subsequently adjacent S1 (Q-S1 or R-S1 interval);
   b) Systolic Interval (SI), measured as the time interval between a Q or R-wave and the subsequently adjacent S2 (Q-S2 or R-S2 interval);
   c) Diastolic interval (DI), measured as the time interval between S2 and the subsequently adjacent Q or R-wave (S2-Q or S2-R interval); and
   d) Left ventricular ejection time (LVET), measured as the time interval between the S1 and the subsequently adjacent S2 (S1-S2 interval).

In various embodiments, parameter generator 532 can generate the amplitude of S1 and/or the cardiac time intervals using the one or more heart sound signals sensed and processed by heart sound sensor 526C, heart sound sensing circuit 528C, and heart sound detector 530C and/or the one or more heart sound signals sensed and processed by heart sound sensor 526C, heart sound sensing circuit 528C, and heart sound detector 530C and the one or more cardiac signals sensed and processed by cardiac sensing electrodes 526A, cardiac sensing circuit 528A, and cardiac events detector 530A.

(4) Heart rate variability (HRV) parameter, such as:
   a) Ratio of low-frequency (LF) HRV to high-frequency (HF) HRV spectral power (LF/HF ratio). The LF HRV includes components of the HRV having frequencies between about 0.04 Hz and 0.15 Hz. The HF HRV includes components of the HRV having frequencies between about 0.15 Hz and 0.40 Hz.

HRV is the beat-to-beat variance in cardiac cycle length over a period of time. An "HRV parameter" as used in this document includes any parameter being a measure of the HRV and used as a baroreflex parameter, including any qualitative expression of the beat-to-beat variance in cardiac cycle length over a period of time. Due to the significant impact of respiration on HRV, parameter generator 532 may calculate an HRV parameter, such as the LF/HF ratio, during times when values of the one or more respiratory parameters are consistent within specified ranges, and/or normalized the HRV parameter by the one or more respiratory parameters to improve algorithm robustness. In various embodiments, parameter generator 532 can generate the HRV parameter using the one or more cardiac signals sensed and processed by cardiac sensing electrodes 526A, cardiac sensing circuit 528A, and cardiac events detector 530A. When the HRV parameter is to be corrected or normalized by respiration, parameter generator 532 can generate the HRV parameter using the one or more cardiac signals sensed and processed by cardiac sensing electrodes 526A, cardiac sensing circuit 528A, and cardiac events detector 530A and the one or more respiratory signals sensed and processed by respiratory sensor 526D, respiratory sensing circuit 528D, and respiratory parameter detector 530D.

(5) Slope of change in the heart rate, or time interval during which the peak of the heart rate changes by a specified percentage, during a change in the posture (e.g., laying/sitting to standing or standing to laying/sitting). The heart rate should increase when the patient's posture changes from laying/sitting to standing and decrease when the patient's posture changes from standing to laying/sitting, and the slope or rate of the change in the heart rate indicates change in the BRS. In various embodiments, parameter generator 532 can generate the slope of change in the heart rate using the one or more cardiac signals sensed and processed by cardiac sensing electrodes 526A, cardiac sensing circuit 528A, and cardiac events detector 530A.

(6) Slope of change in the blood pressure (as sensed directly using pressure sensor 526B or sensed directly through a surrogate such as using heart sound sensor 526C), or time interval during which the peak of the blood pressure changes by a specified percentage, during a change in the posture (e.g., laying/sitting to standing or standing to laying/sitting). The blood pressure should increase when the patient's posture changes from laying/sitting to standing and decrease when the patient's posture changes from standing to laying/sitting, and the slope or rate of the change in the blood pressure indicates change in the BRS. In various embodiments, parameter generator 532 can generate the blood pressure (or its surrogates) using the one or more pressure signals sensed and processed by pressure sensor 526B, pressure sensing circuit 528B, and pressure feature detector 530B and/or the one or more heart sound signals sensed and processed by heart sound sensor 526C, heart sound sensing circuit 528C, and heart sound detector 530C.

(7) Slope or strength of the linear association between the blood pressure (as sensed directly using pressure sensor 526B or sensed directly through a surrogate such as using heart sound sensor 526C) and the IBI (e.g., R-R interval). The cross-correlations (in time domain) and coherence (in frequency domain) may be used to improve the algorithm used by parameter generator 532 to calculate the one or more baroreflex parameters and/or by pain analyzer 310 to produce the signal metric and/or the pain score. To establish the causality between the relationship (to reduce false positives), for example, Granger causality may be incorporated. In various embodiments, parameter generator 532 can generate the slope or strength of the linear association between the blood pressure and the IBI using the one or more pressure signals sensed and processed by pressure sensor 526B, pressure sensing circuit 528B, and pressure feature detector 530B and the one or more cardiac signals sensed and processed by cardiac sensing electrodes 526A, cardiac sensing circuit 528A, and cardiac events detector 530A, and/or the one or more heart sound signals sensed and processed by heart sound sensor 526C, heart sound sensing circuit 528C, and heart sound detector 530C and the one or more cardiac signals sensed and processed by cardiac sensing electrodes 526A, cardiac sensing circuit 528A, and cardiac events detector 530A

(8) Neural activity parameter, such as a parameter representative of neural traffic, derived from one or more neural signals recorded from one or more target nerves that relay blood pressure information to the patient's brainstem (e.g., neural sensing electrodes 526E placed around, on, or adjacent vagal and/or glossopharyngeal nerves). In various embodiments, parameter generator 532 can generate the neural activity parameter using the one or more neural signals sensed and processed using neural sensing electrodes 526E, neural sensing circuit 528E, and neural events detector 530E.

(9) Other one or more parameters being measures of BRS. Examples (1)-(8) are discussed as specific examples, rather than limitations, of the one or more baroreflex parameters. Any parameter allowing for measurement of BRS can be used as a baroreflex parameter, in various embodiments. In various embodiments, parameter generator 532 can generate the other one or more parameters using additional sensor(s) 536, additional sensing circuit(s) 538, and additional feature detector(s) 540.

In various embodiments, any one or any combination of the parameters discussed in the examples (1)-(9) above can be selected for use as the one or more baroreflex parameters to be produced by parameter generator 532. The selection can be made by considering factors such as the desired accuracy and/or reliability of the signals to be sensed, complexity and/or risk involved in placing the sensor(s) (which may depend on the location of each system components placed (e.g., implanted in the patient), power consumption, complexity of computation, and cost. Examples of selection of the one or more baroreflex parameters can include any one or any combination of the examples (1)-(9).

In some embodiments, for efficiency of memory use and computation, capture or storage of a rolling window of data can be triggered by an event of interest (e.g., a posture change), as controlled by posture sensing circuit 422, each of baroreflex sensing circuit 528, and/or additional sensing circuit(s) 538. This rolling window can temporally cover the event, such as starting about 1 second prior to the event and ending about 1 second after the event, to allow sufficient information to be analyzed by pain analyzer 310 on a few heart beats (see, e.g., FIG. 1B), or a wider range of time as needed. In some embodiments, sampling rate applied to any signal sensed by a sensor illustrated in FIG. 5 can be increased upon occurrence of the event of interest. In some embodiments, for power and computation efficiency, the analysis by pain analyzer 310 can be updated periodically (such as on a beat-by-beat or second-by-second basis), or upon occurrence of the event of interest. In some embodiments, for power and computation efficiency, a low-power operation mode can be used, for example when the patient is known to be sleeping or at rest. The low-power operation mode can allow for low sampling rate, less frequency analysis, etc., to conserve power. In some embodiments, the weighting factors used by parameter analyzer 312 can be changed for a specified period of time after occurrence of the event of interest. In some embodiments, pain score generator 314 can generate an acute pain score based on the parameters for a specified time around occurrences of the event of interest and a chronic pain score based on the parameters for a longer period of time, thereby distinguishing acute pain from chronic pain.

Figure 6:
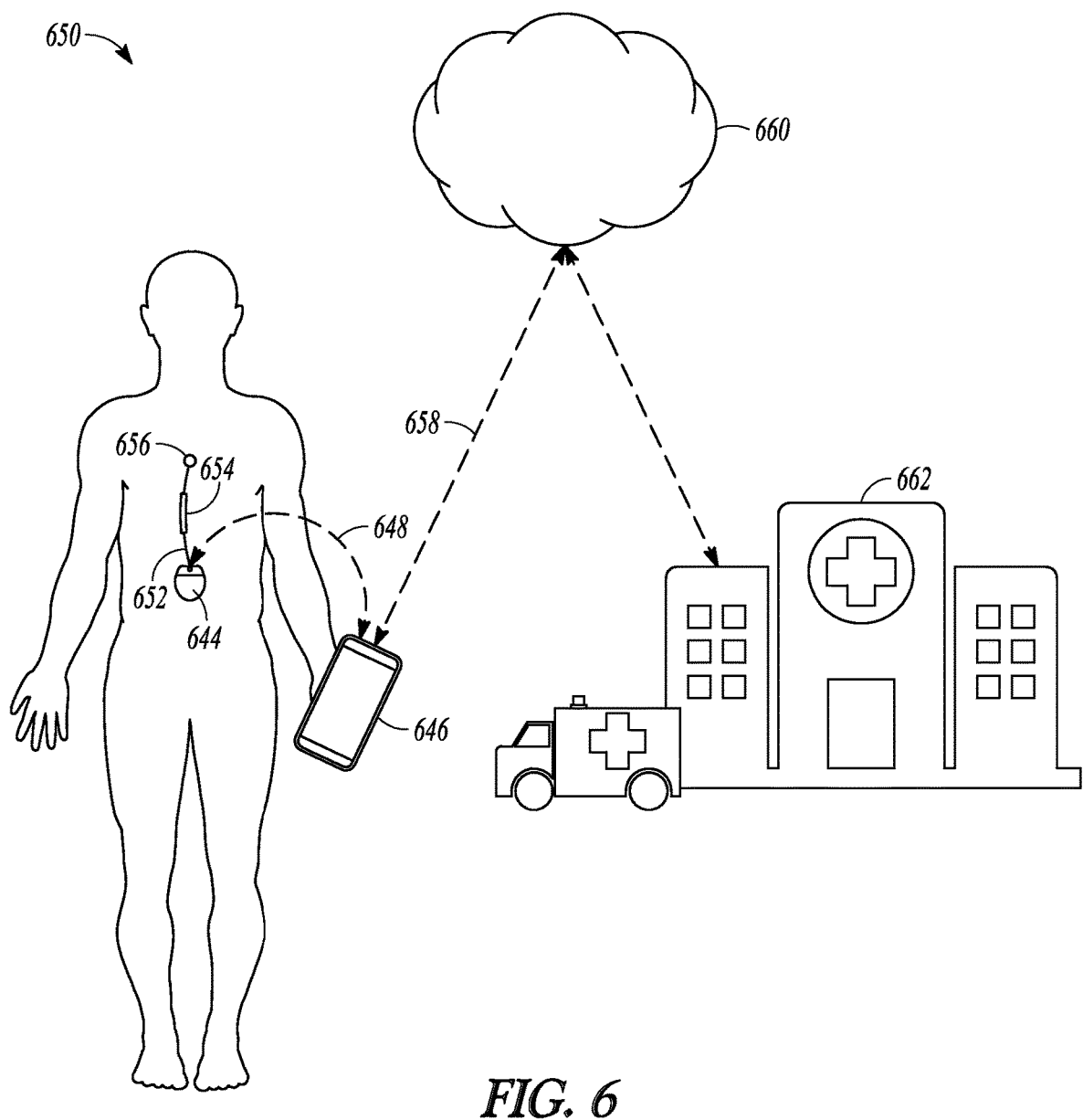
FIG. 6 illustrates an embodiment of a pain management system, such as one in which the pain management system of FIG. 2 may be implemented, and portions of an environment in which the pain management system may be used.

FIG. 6 illustrates a pain management system 650 and portions of an environment in which system 650 may be used. System 200 can be implemented in system 650. System 650 can include an implantable medical device 644, an implantable lead or lead system 652 connected to implantable medical device 644, a portable device 646 communicatively coupled to implantable medical device 644 via a wireless communication link 648, a network 660 communicatively coupled to portable device 646 via communication link 658, and medical facility 662 communicatively coupled to network 660. A pain monitoring circuit such as pain monitoring circuit 202 (including its various embodiments) can be contained within implantable medical device 644 or distributed in implantable medical device 644 and portable device 646. Implantable medical device 644 can include a therapy device such as pain relief device 206 to deliver one or more pain relief therapies. In various embodiments, portable device 646 can be implemented as a dedicated device or in a generic device such as a smartphone, a laptop computer, or a tablet computer. In various embodiments, system 200, including the various embodiments of its elements discussed in this document, can be implemented entirely in implantable medical device 644 only, implemented in both implantable medical device 644 and portable device 646, or implemented in implantable medical device 644, portable device 646, and other one or more components of system 650.

In FIG. 6, lead or lead system 652 includes an electrode or electrode array 654 and a sensor 656 as illustrated by way of example, but not by way of restriction. In various embodiments, additional one or more electrodes can be incorporated onto implantable medical device 644. In the illustrated embodiment, sensor 656 can represent an embodiment of a sensor (e.g., heart sound sensor 526C) that is incorporated into lead or lead system 652 and to be positioned in or near the thoracic region. In another embodiment, the sensor (e.g., heart sound sensor 526C) can be embedded in implantable medical device 644, which can be placed in the lumbar region (e.g., for delivering SCS). In various embodiments, each of the one or more posture sensors, the one or more baroreflex sensors, and the one or more additional sensors as discussed in this document (with reference to FIGS. 4 and 5) can be incorporated into lead or lead system 652, included in implantable medical device 644, or implemented as separate device, such as an implantable device, that can communicate with implantable medical device 644 wirelessly via telemetry.

In various embodiments, the pain score as well as other data can be produced by implantable medical device 644 based on sensed signals and transmitted to portable device 646 via communication link 648. Portable device 646 can relay the pain score as well as the other data to network 660 via communication link 658 to be stored, further analyzed, inform the patient's healthcare provider, and/or used to control delivery of one or more pain relief therapies from implantable medical device 644. When the pain score and/or the other data indicate that the patient needs medical attention, such as when system 650 is unable to automatically adjust the one or more pain relief therapies for a satisfactory result as indicated by the composite pain score, a notification will be transmitted to medical facility 662 from network 660.

In various embodiments, portable device 646 and one or more devices within network 660 and/or medical facility 662 can allow a user such as a physician or other caregiver and/or the patient to communicate with implantable medical device 644, for example to initialize and adjust settings of implantable medical device 644. For example, the portable device may inform the patient the pain score and/or other information produced by implantable medical device 644, and allow the patient to turn implantable medical device 644 on and off and/or adjust certain patient-programmable parameters controlling delivery of a pain-relief therapy.

The sizes and shapes of the elements of system 650 and their locations relative to the patient's body are illustrated by way of example and not by way of restriction. System 650 is discussed as a specific application of pain management according to various embodiments of the present subject matter. In various embodiments, the present subject matter may be applied in any type of pain management in controlling delivery of one or more pain relief energy and/or agents.

Figure 7:
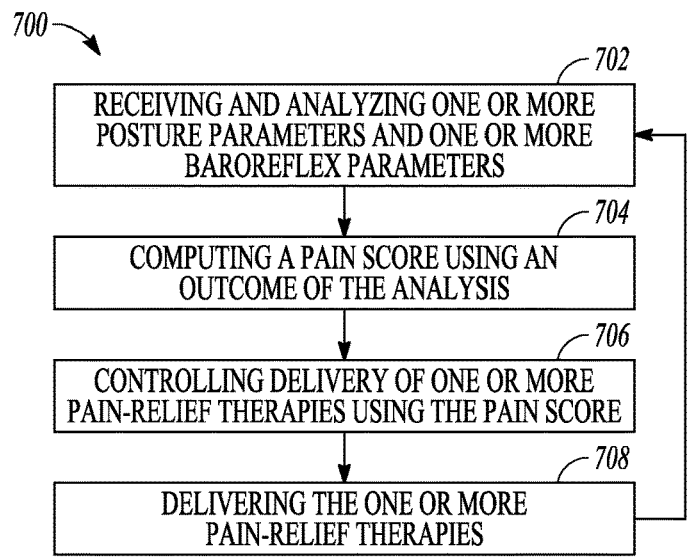
FIG. 7 illustrates an embodiment of a method for pain management.

FIG. 7 illustrates an embodiment of a method 700 for pain management. In one embodiment, system 200, including the various embodiments of its components, is configured (e.g., programmed) to perform method 700.

At 702, one or more posture parameters and one or more baroreflex parameters are received and analyzed. The one or more posture parameters are indicative of posture of a patient. The one or more baroreflex parameters allow for determination of BRS of the patient. Examples of the one or more posture parameters and the one or more baroreflex parameters include the parameters that can be generated by parameter generator 432 or 532.

At 704, a pain score is computed using an outcome of the analysis at 702. The pain score is a function of the one or more posture parameters and the one or more baroreflex parameters, and is indicative of a degree (intensity) of the pain.

At 706, delivery of the one or more pain-relief therapies is controlled using the pain score and therapy parameters. In various embodiments, the one or more posture parameters and the one or more baroreflex parameters are continuously or periodically received and analyzed to update the pain score to provide feedback control on the delivery of the one or more pain-relief therapies.

At 708, the one or more pain-relief therapies are delivered to the patient. Examples of the one or more pain-relief therapies include those deliverable from pain relief device 206.

Figure 8:
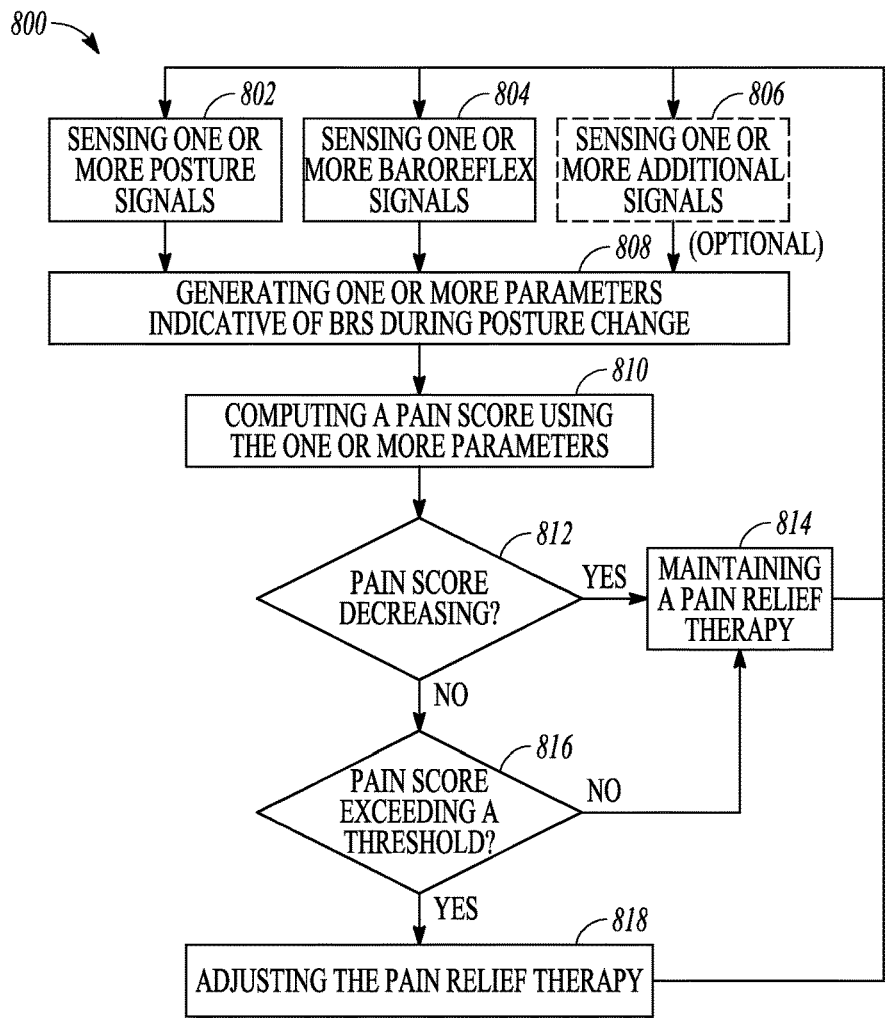
FIG. 8 illustrates another embodiment of a method for pain management.

FIG. 8 illustrates an embodiment of a method 800 for pain management. In one embodiment, system 200, including the various embodiments of its components, is configured (e.g., programmed) to perform method 800.

At 802, one or more posture signals are sensed. Examples of the one or more posture signals include the one or more posture signals that can be sensed using posture sensor(s) 420.

At 804, one or more baroreflex signals are sensed. Examples of the one or more baroreflex signals include the one or more baroreflex signals that can be sensed using baroreflex sensor(s) 426 or 526.

Optionally at 806, one or more additional signals are sensed. In various embodiments, the one or more additional signals may be directly indicative of the BRS but otherwise relate to pain. Examples for such one or more additional signals are discussed in U.S. Provisional Patent Application Ser. No. 62/400,336.

At 808, one or more parameters indicative of BRS during posture change are generated. Examples of the one or more parameters include the one or more posture parameters and the one or more baroreflex parameters that can be generated using parameter generator 432 or 532. In some embodiments, the one or more parameters also include one or more physiological parameters each indicative of a physiological function or state of the patient, one or more functional parameters each indicative of a physical activity or state of the patient, and/or one or more patient parameters including subjective information provided by the patient, in addition to using the one or more posture parameters and the one or more baroreflex parameters, that can be generated using parameter generator 432 or 532. In one embodiment, a BRS signal metric is generated using the one or more posture parameters and the one or more baroreflex parameters, and optionally the one or more additional parameters. The BRS signal metric is representative of the BRS of the patient being a function of a change in the posture of the patient.

At 810, a pain score is computed using the one or more parameters generated at 808. The pain score is an objective and quantitative measure of a degree (intensity) of pain. In one embodiment, the pain score is computed using the BRS signal metric. In one embodiment, an acute pain score is generated to indicate acute pain, such as around occurrence of an event of interest, and a chronic pain score is also generated to indicate chronic pain.

At 812, whether the pain score is decreasing (indicating decreasing intensity of pain) is determined. If the pain score is decreasing, delivery of a pain relief therapy is maintained (i.e., the pain relief therapy is not started, stopped, or adjusted in response) at 814. If the pain score is not decreasing, whether the pain score exceeds a specified therapy threshold is determined at 816. If the pain score does not exceed the specified therapy threshold, the delivery of the pain relief therapy is maintained (i.e., the pain relief therapy is not started, stopped, or adjusted in response) at 814. If the pain score exceeds the specified therapy threshold, the pain relief therapy is adjusted, such as optimized. In various embodiments, the optimization can include adjusting the therapy parameters towards improving BRS measures (e.g., as indicated by the BRS signal metric or the pain score). In one embodiment, the optimization includes adjusting the therapy parameters to minimizing the value of the pain score (i.e., to minimizing the intensity of the pain). In one embodiment in which the acute pain score is generated at 810, the adjustment of the pain relief therapy at 818 can be applied temporarily. In one embodiment, if a history of acute pain occurring upon specific posture change(s) has been established for the patient (automatically and/or by a physician, other caregiver, and/or the patient), the adjustment of the pain relief therapy at 818 can be enabled or mandated upon detection of such specific posture change(s).

In various embodiments, method 800 is performed continuously for adjusting the pain relief therapy when such therapy is being applied to the patient. In various embodiments, method 800 is performed periodically for adjusting the pain relief therapy when such therapy is being applied to the patient. In various embodiments, method 800 is performed in response to a user command entered by the patient or a user such as a physician or other caregiver, such as when the pain intensifies as perceived by the patient.

In various embodiments, a pain management system, such as systems 200 or 650, may include any one or any combination of the physical and functional structures discussed above and/or one or more other physical and functional structures configured to be used to monitor and control pain for a patient. In addition to the Examples discussed in the Summary section above, non-limiting examples 1-25 for pain management using BRS during posture change are provided as follows:

In Example 1, a system for providing a patient with pain management may include a pain monitoring circuit. The pain monitoring circuit may include a parameter analyzer circuitry and pain score generator circuitry. The parameter analyzer circuitry may be configured to receive and analyze one or more posture parameters indicative of posture of the patient and one or more baroreflex parameters allowing for determination of baroreflex sensitivity (BRS) of the patient. The pain score generator circuitry may be configured to compute a pain score using an outcome of the analysis. The pain score being a function of the one or more posture parameters and the one or more baroreflex parameters and indicative of a degree of pain.

In Example 2, the subject matter of Example 1 may optionally be configured to further include a pain relief device configured to deliver one or more pain-relief therapies to the patient and a control circuit configured to control the delivery of the one or more pain-relief therapies using the pain score.

In Example 3, the subject matter of any one or any combination of Examples 1 and 2 may optionally be configured such that the parameter analyzer circuitry is configured to generate a BRS signal metric using the one or more posture parameters and the one or more baroreflex parameters, and the pain score generator circuitry is configured to compute the pain score using the BRS signal metric. The BRS signal metric is representative of the BRS of the patient being a function of a change in the posture of the patient.

In Example 4, the subject matter of Example 3 may optionally be configured such that the parameter analyzer circuitry is configured to generate the BRS signal metric using the one or more posture parameters, the one or more baroreflex parameters, and at least one parameter selected from a physiological parameter indicative of a physiological function or state of the patient, a functional parameter indicative of a physical activity or state of the patient, or a patient parameter including subjective information provided by the patient.

In Example 5, the subject matter of any one or any combination of Examples 1 to 4 may optionally be configured such that the one or more posture parameters include a parameter indicative of a type of the change in the posture of the patient, and the parameter analyzer circuitry is configured to generate the BRS signal metric representative of the BRS of the patient being a function of the type of the change in the posture of the patient.

In Example 6, the subject matter of any one or any combination of Examples 1 to 5 may optionally be configured such that the one or more posture parameters include one or more parameters indicative of one or more of a magnitude or a duration of the change in the posture of the patient, and the parameter analyzer circuitry is configured to generate the BRS signal metric representative of the BRS of the patient being a function of the one or more of the magnitude or the duration of the change in the posture of the patient.

In Example 7, the subject matter of any one or any combination of Examples 1 to 6 may optionally be configured such that the one or more posture parameters include one or more parameters indicative of one or more of a velocity or an acceleration of the change in the posture of the patient, and the parameter analyzer circuitry is configured to generate the BRS signal metric representative of the BRS of the patient being a function of the one or more of the velocity or the acceleration of the change in the posture of the patient.

In Example 8, the subject matter of any one or any combination of Examples 1 to 7 may optionally be configured such that the pain monitoring circuit further include one or more posture sensors configured to sense one or more posture signals indicative of posture of the patient, a posture sensing circuit configured to process the one or more posture signals, a posture feature detector configured to detect one or more posture signal features using the processed one or more baroreflex signals, and a parameter generator configured to generate the one or more posture parameters using the detected one or more posture signal features.

In Example 9, the subject matter of Example 8 may optionally be configured such that the pain monitoring circuit further include one or more baroreflex sensors configured to sense one or more baroreflex signals allowing for the determination of the BRS, a baroreflex sensing circuit configured to process the sensed one or more baroreflex signals, and a baroreflex feature detector configured to detect one or more baroreflex signal features using the processed one or more baroreflex signals, and such that the parameter generator is further configured to generate the one or more baroreflex parameters using the detected one or more baroreflex signal features.

In Example 10, the subject matter of Example 9 may optionally be configured such that the parameter generator is configured to generate a heart rate or a change of the heart rate of the one or more baroreflex parameters.

In Example 11, the subject matter of any one or any combination of Examples 9 and 10 may optionally be configured such that the baroreflex parameter generator is configured to generate a blood pressure or a change of the blood pressure of the one or more baroreflex parameters. The blood pressure is an actual blood pressure of the patient or a surrogate of the blood pressure of the patient.

In Example 12, the subject matter of Example 11 may optionally be configured such that the baroreflex parameter generator is configured to generate an amplitude of second heart sounds, S2, or a pulse transit time, PTT, as the surrogate of the blood pressure of the patient.

In Example 13, the subject matter of any one or any combination of Examples 9 to 12 may optionally be configured such that the baroreflex parameter generator is configured to generate a heart sound parameter of the one or more baroreflex parameters. The heart sound parameter is representative of an amplitude of a heart sound or a time interval associated with the heart sound.

In Example 14, the subject matter of any one or any combination of Examples 9 to 13 may optionally be configured such that the baroreflex parameter generator is configured to generate a heart rate variability parameter of the one or more baroreflex parameters, the heart rate variability parameter being a measure of heart rate variability of the patient.

In Example 15, the subject matter of any one or any combination of Examples 9 to 14 may optionally be configured such that the baroreflex parameter generator is configured to generate a neural parameter of the one or more baroreflex parameters. The neural parameter is indicative of neural activities associated relaying information about blood pressure of the patient.

In Example 16, a method for managing pain of a patient is provided. The method may include: receiving and analyzing one or more posture parameters indicative of posture of the patient and one or more baroreflex parameters allowing for determination of a baroreflex sensitivity (BRS) of the patient, and computing a pain score using an outcome of the analysis. The pain score is a function of the one or more posture parameters and the one or more baroreflex parameters and indicative of a degree of the pain.

In Example 17, the subject matter of Example 16 may optionally further include: delivering one or more pain-relief therapies to the patient from a pain relief device, and controlling the delivery of the one or more pain-relief therapies using the pain score.

In Example 18, the subject matter of analyzing the one or more posture parameters and the one or more baroreflex parameters as found in any one or any combination of Examples 16 and 17 may optionally further include generating a BRS signal metric using the one or more posture parameters and the one or more baroreflex parameter. The BRS signal metric is representative of the BRS of the patient being a function of a change in the posture of the patient. The subject matter of computing the pain score as found in any one or any combination of Examples 16 and 17 may optionally further include computing the pain score using the BRS signal metric.

In Example 19, the subject matter of generating the BRS signal metric as found in Example 18 may optionally further include generating the BRS signal metric using the one or more posture parameters, the one or more baroreflex parameters, and at least one parameter selected from a physiological parameter indicative of a physiological function or state of the patient, a functional parameter indicative of a physical activity or state of the patient, or a patient parameter including subjective information provided by the patient.

In Example 20, the subject matter of any one or any combination of Examples 16 to 19 may optionally further include: sensing one or more posture signals indicative of posture of the patient using one or more posture sensors implanted in the patient, and generating the one or more posture parameters using the one or more posture signals.

In Example 21, the subject matter of the one or more posture parameters as found in any one or any combination of Examples 16 to 20 may optionally further include one or more of a parameter indicative of a type of the change in the posture of the patient, a parameter indicative of a magnitude of the change in the posture of the patient, a parameter indicative of a duration of the change in the posture of the patient, a parameter indicative of a velocity of the change in the posture of the patient, or a parameter indicative of an acceleration of the change in the posture of the patient.

In Example 22, the subject matter of any one or any combination of Examples 16 to 21 may optionally further include: sensing one or more baroreflex signals allowing for the determination of the BRS using one or more baroreflex sensors implanted in the patient, and generating the one or more baroreflex parameters using the one or more baroreflex signals.

In Example 23, the subject matter of the one or more baroreflex signals as found in Example 22 may optionally further include one or more of a cardiac signal indicative of a heart rate of the patient or a blood pressure signal indicative of a blood pressure of the patient.

In Example 24, the subject matter of the one or more baroreflex parameters as found in Example 23 may optionally further include a parameter indicative of one or more of a heart rate, a change in the heart rate, a slope of change in the heart rate, or a heart rate variability.

In Example 25, the subject matter of the one or more baroreflex parameters as found in Example 23 may optionally further include a blood pressure parameter, a change in the blood pressure parameter, a slope of the change in the blood pressure parameter, or a measure of a neural activity driven by the blood pressure or the change in the blood pressure, the blood pressure parameter indicative of the blood pressure of the patient.

Example: Pain Management Using Ambulatory Monitoring of Spontaneous BRS

In various embodiments, an exemplary system can provide for ambulatory assessment of BRS. BRS varies as a natural response to various factors including respiration, physical stressors, and mental stressors in daily activities. Variability in BRS can be used as an indicator of baroreceptor function and used as an objective measure of pain. Dynamic changes in baroreflex function can be captured using beat-to-beat sensitivity to analyze changes in heart rate and blood pressure for each cardiac contraction.

One indicator of the baroreflex function is spontaneous BRS, which is the spontaneous changes in BRS measured as beat-to-beat sensitivity. Spontaneous BRS can be measured through consecutive heart beats that are characterized by simultaneous increase or decrease in blood pressure and cardiac interval (e.g., time interval between successive R-waves). BRS can be calculated as the average of the linear regression slopes detected for each sequence of the simultaneous increase or decrease in blood pressure and cardiac interval over a given time interval. In various embodiments, such sequences of simultaneous increase or decrease in blood pressure and cardiac interval can be captured by monitoring respiration and/or physical activity in a patient. While physical activity and respiration monitoring are discussed as examples, any other signals allowing for capturing dynamic spontaneous BRS can be applied without departing from the scope of the present subject matter.

Similar to respiratory sinus arrhythmia (RSA) and diminished heart rate variability (HRV), diminished BRS is evident in chronic pain patients. Because there is a spontaneous blood pressure variability due to respiration, dynamic spontaneous BRS can be captured by analyzing blood pressure and heart rate during a respiratory cycle. Respiration induces HRV by modulation of the arterial baroreflex and by direct mechanical modulation of the sinoatrial (SA) node pacemaker properties. Using inspiration and expiration, consecutive increases or decreases in blood pressure and cardiac interval can be captured to calculate BRS in the patient.

Moment-to-moment regulation of blood pressure through the baroreceptor reflex is reduced during exercise when compared to rest. BRS decreases during exercise because the body's operating point on the heart rate-blood pressure curve shifts away from the maximal sensitivity point at the center of the curve (at rest condition). The shift moves the "set point" of blood pressure to a higher level with less sensitivity to changes in blood pressure. This change in BRS varies with exercise intensity. As the exercise level increases, the operating point progressively moves away from the center point towards the upper threshold of the heart rate-blood pressure curve. Chronic pain is associated with alterations in autonomic function, which can be analyzed by monitoring baroreflex function during physical activity. Exercise alone can cause a decrease in BRS, and exercise compounded with chronic pain can lead to a more significant decrease in BRS. In a study using a mouse chronic musculoskeletal pain model, the autonomic dysfunction was prevented in mice that exercised compared to those that did not. By coupling activity and BRS monitoring, it is possible to investigate the baroreceptor reflex at a higher operator point (due to exercise) and evaluate therapeutic interventions.

Thus, the present system uses baroreceptor response to events such as respiration or physical activity of the patient to determine an objective marker of pain that can be continuously captured during every day activities. This objective marker of pain, such as a pain score, can be used to guide diagnoses and therapeutic interventions. The system can include one or more sensors, such as sensors allowing for ambulatory blood pressure and heart rate monitoring, for measuring BRS and one or more sensors for sensing physical activity and/or respiration. Spontaneous BRS can be analyzed during physical activity as detected by an activity sensor and/or analyzed during respiration as detected by the respiratory sensor. An objective pain score can be determined based on the analysis. The system can also allow for monitoring of spontaneous BRS at home to provide an indicator of the patient's state and efficacy of therapeutic interventions.

Referring to FIG. 3 again, in various embodiments using ambulatory monitoring of spontaneous BRS for pain management, parameter analyzer 312 can receive and analyze one or more activity parameters and/or one or more respiratory parameters and the one or more baroreflex parameters. In various embodiments, the one or more activity parameters are indicative of a level of physical activity of the patient. The one or more respiratory parameters are indicative of respiratory cycles (each including an inspiratory phase and an expiratory phase) of the patient. The one or more baroreflex parameters can include any one or more signals indicative of the patient's baroreflex and allow for determination of the BRS. Pain score generator 314 can compute a pain score using an outcome of the analysis. The pain score indicating of a degree (intensity) of the pain. In one embodiment, parameter analyzer 312 detects values of each baroreflex parameter of the one or more baroreflex parameter during time intervals corresponding to, for example, a specified range of the level of physical activity, a specified period during the inspiratory phase, and/or a specified period during the expiratory phase, and stratifies the values of the baroreflex parameter by values of each of the one or more activity parameters and/or one or more respiratory parameters.

In one embodiment, parameter analyzer 312 produces a signal metric being a measure of BRS as a function of the one or more activity parameters and/or one or more respiratory parameters, and pain score generator 314 computes the pain score using the signal metric. In one embodiment, in addition to the one or more activity parameters and/or one or more respiratory parameters and the one or more baroreflex parameters, pain analyzer 310 uses one or more additional parameters to produce the signal metric for an increased reliability of the pain score. The one or more additional parameters can be selected from one or more physiological parameters each indicative of a physiological function or state of the patient, one or more functional parameters each indicative of a physical activity or state of the patient, and/or one or more patient parameters including subjective information provided by the patient. Examples of such one or more additional parameters are discussed in U.S. Provisional Patent Application Ser. No. 62/400,336.

The signal metric can be a linear or nonlinear combination of the one or more baroreflex parameters each as a function of the one or more activity parameters and/or one or more respiratory parameters. In various embodiments, parameter analyzer 312 can produce the signal metric using multiple baroreflex parameters with the weighting factors each applied to one of these baroreflex parameters. In various embodiments, parameter analyzer 312 can adjust the weighting factors through automatic learning and adaptation to the patient over time (e.g., based on stored parameters and/or outcomes of analysis, such as features extracted from the parameters). In various other embodiments, parameter analyzer 312 can allow the weighting factors to be adjusted manually. In various other embodiments, the weighting factors can be adjusted according to a calibration schedule or as needed, and the adjustment can be performed by a user such as a physician or other authorized care provider in a clinic, or initiated by the patient and performed by parameter analyzer 312 automatically at home. In various embodiments, the weighting factors can be patient-specific and dynamically changed based on the patient's conditions and/or activities.

Figure 9:
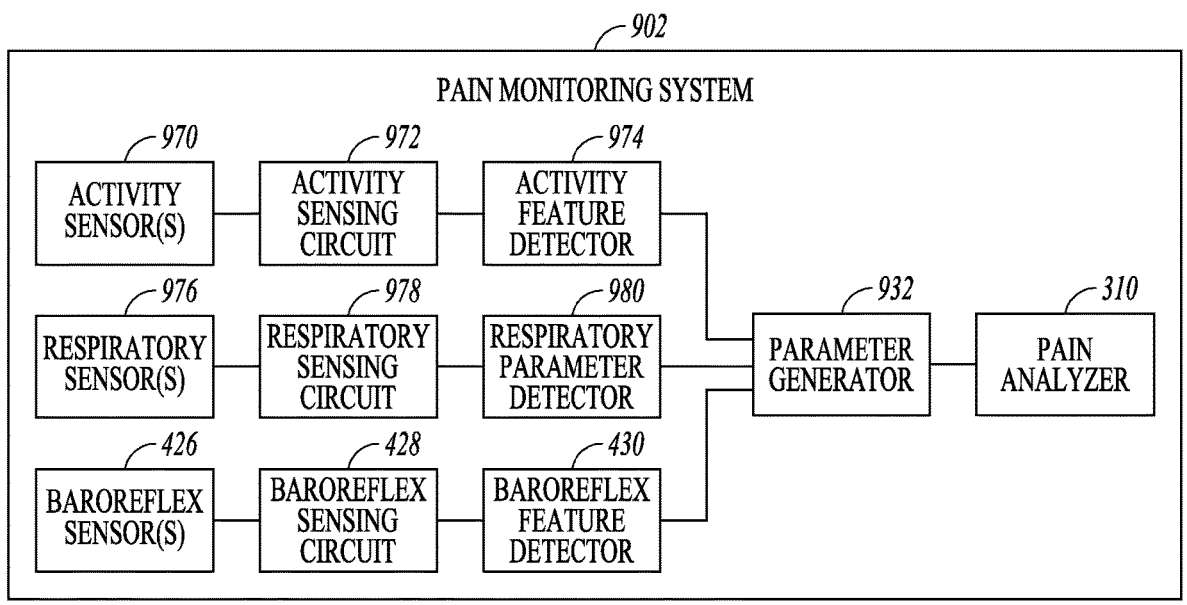
FIG. 9 illustrates another embodiment of the pain monitoring circuit, such as may be used in the pain management system of FIG. 2.

FIG. 9 illustrates an embodiment of a pain monitoring circuit 902, which represent another example of pain monitoring circuit 202. In the illustrated embodiment, pain monitoring circuit 902 can include one or more activity sensors 970, an activity sensing circuit 972, an activity feature detector 974, one or more respiratory sensors 976, a respiratory sensing circuit 978, a respiratory feature detector 980, one or more baroreflex sensors 426, baroreflex sensing circuit 428, baroreflex feature detector 430, a parameter generator 932, and pain analyzer 310. In various embodiments, pain monitoring circuit 902 can use either one or both of the one or more activity parameters and the one or more respiratory parameters in determining the patient's spontaneous BRS. Thus, in one embodiment, pain monitoring circuit 902 includes one or more activity sensors 970, activity sensing circuit 972, activity feature detector 974, one or more baroreflex sensors 426, baroreflex sensing circuit 428, baroreflex feature detector 430, parameter generator 932, and pain analyzer 310. In another embodiment, pain monitoring circuit 902 includes one or more respiratory sensors 976, respiratory sensing circuit 978, respiratory feature detector 980, one or more baroreflex sensors 426, baroreflex sensing circuit 428, baroreflex feature detector 430, parameter generator 932, and pain analyzer 310.

In various embodiments, activity sensor(s) 970 can sense one or more activity signals indicative of the level of physical activity of the patient. Examples of the activity sensor(s) 970 include an accelerometer a gyroscope, a magnetometer, an electromyography (EMG) sensor, a global positioning system (GPS), or any other sensor or combination of sensors capable of providing one or more activity signals allowing for determination of the patient's level of physical activity. Activity sensing circuit 972 can process the one or more activity signals. Activity feature detector 974 can detect one or more activity signal features using the processed one or more activity signals. The one or more activity signal features allow for measurement of the one or more activity parameters. Parameter generator 932 can generate the one or more activity parameters using the detected one or more activity signal features. In various embodiments, the one or more activity parameters include at least a level of physical activity of the patient. In various embodiments, the one or more activity parameters can also include one or more parameters each indicative a type of physical activity or a level of that type of physical activity.

Respiratory sensor(s) 976 can sense one or more respiratory signals. Respiratory sensing circuit 978 can process the sensed one or more respiratory signals. Respiratory parameter detector 980 can detect one or more respiratory parameters using the processed sensed one or more respiratory signals. The one or more respiratory signals are physiologic signals indicative of respiratory cycles and various other respiratory parameters. Various embodiments of respiratory sensor 526D, respiratory sensing circuit 528D, and respiratory parameter detector 530D, as discussed above with reference to FIG. 5, are also applicable as various embodiments for respiratory sensor(s) 976, respiratory sensing circuit 978, and respiratory parameter detector 980, respectively.

Various embodiments of baroreflex sensor(s) 426, baroreflex sensing circuit 428, and baroreflex feature detector 430, including baroreflex sensors 526 (A-E), baroreflex sensing circuits 528 (A-E), and baroreflex feature detectors 530 (A-E) are discussed above with reference to FIG. 5. In various embodiments, activity sensor(s) 970 (if used), respiratory sensor(s) 976 (if used), and baroreflex sensor(s) 426 can each be configured as an external (such as wearable) sensor or an implantable sensor.

Parameter generator 932 can generate the one or more baroreflex parameters each being a measure of the BRS using the one or more signal features detected by baroreflex feature detector 430 (including its various embodiments such as baroreflex feature detectors 530. In some embodiments, parameter generator 932 can further generate the one or more additional parameters. In various embodiments, the one or more baroreflex parameters generated by parameter generator 932 can include, but are not limited to, the same examples (1)-(9), including their various combinations, discussed above as the one or more baroreflex parameters generated by parameter generator 532.

In various embodiments, parameter generator 932 can generate one or more timing parameters and one or more baroreflex parameters allowing for determination of baroreflex sensitivity (BRS) of the patient. The one or more timing parameters are indicative of time intervals during which values of the one or more baroreflex parameters are used to determine the BRS. The one or more timing parameters are indicative of simultaneous increase or decrease in blood pressure and cardiac interval of the patient. Examples of the one or more timing parameters include the one or more activity parameters and the one or more respiratory parameters as discussed above.

In various embodiments, parameter generator 932 can classify the BRS based on the level of physical activity or exertion indicated by the one or more activity signals and/or the one or more respiratory signals. The level of physical activity can include discrete levels such as mild activity, moderate activity, and vigorous activity. The level of physical activity can also be over a continuum of levels indicated by signals such as activity, respiration, and/or biochemical markers, for example, and by vector magnitude units over a period of time, caloric expenditure, distance traveled, or other activity or exertion measures, or a combination of such measures.

In various embodiments, pain analyzer 310 can calculate the pain score as an objective measure of therapeutic efficacy from the spontaneous BRS assessed throughout changes in the level of physical activity or respiration. In some embodiments, the pain score can be calculated based on the spontaneous BRS and one or more additional parameters (i.e., the one or more physiological parameters, the one or more functional parameters, and/or the one or more patient parameters, with examples discussed in U.S. Provisional Patent Application Ser. No. 62/400,336). The pain score can be used to quantify pain for diagnostic and/or monitoring purposes as well as therapy control. For example, the pain score can be used to indicate therapeutic efficacy for determining optimal therapy parameters or in a closed-loop therapy to treat chronic pain or related disorders.

Figure 10:
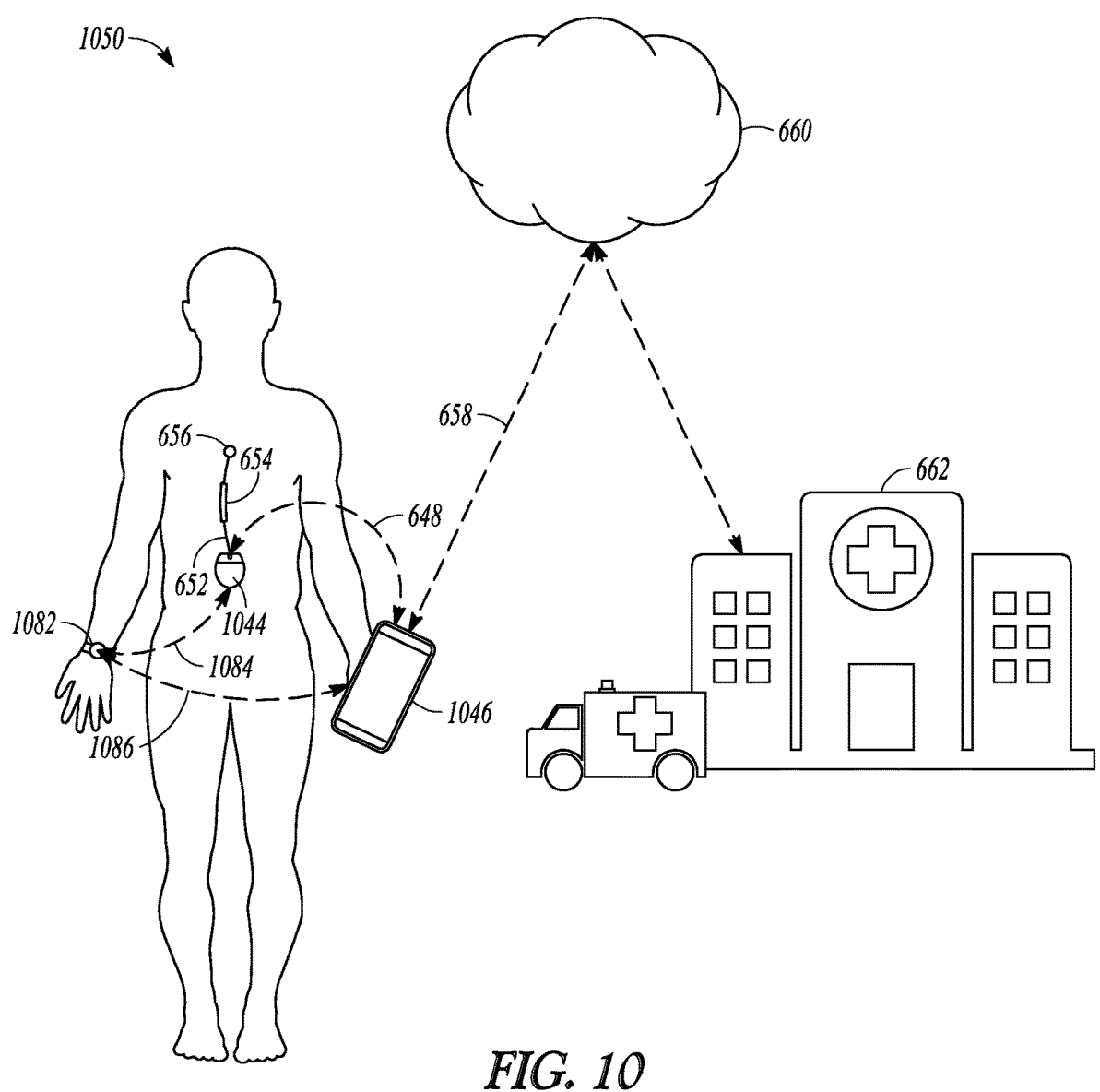
FIG. 10 illustrates another embodiment of a pain management system, such as one in which the pain management system of FIG. 2 may be implemented, and portions of an environment in which the pain management system may be used.

FIG. 10 illustrates a pain management system 1050 and portions of an environment in which system 1050 may be used. System 200 can be implemented in system 1050. System 650 can include an implantable medical device 1044, implantable lead or lead system 652 connected to implantable medical device 1044, a portable device 1046 communicatively coupled to implantable medical device 1044 via a wireless communication link 648, a wearable sensor 1082 communicatively coupled to implantable medical device 1044 via a wireless communication link 1084 and communicatively coupled to portable device 1046 via a wireless communication link 1086, a network 660 communicatively coupled to portable device 1046 via communication link 658, and medical facility 662 communicatively coupled to network 660. A pain monitoring circuit such as pain monitoring circuit 202 (including its various embodiments) can be contained within implantable medical device 1044 or distributed in implantable medical device 1044 and portable device 1046. Implantable medical device 1044 can include a therapy device such as pain relief device 206 to deliver one or more pain relief therapies. In various embodiments, portable device 1046 can be implemented as a dedicated device or in a generic device such as a smartphone, a laptop computer, or a tablet computer. In various embodiments, system 200, including the various embodiments of its elements discussed in this document, can be implemented entirely in implantable medical device 1044 only, implemented in both implantable medical device 1044 and portable device 1046, or implemented in implantable medical device 1044, portable device 1046, and other one or more components of system 1050.

Lead or lead system 652 includes an electrode or electrode array 654 and a sensor 656 as illustrated by way of example, but not by way of restriction. In various embodiments, additional one or more electrodes can be incorporated onto implantable medical device 1044. In the illustrated embodiment, sensor 656 can represent an embodiment of a sensor (e.g., heart sound sensor 526C) that is incorporated into lead or lead system 652 and to be positioned in or near the thoracic region. In another embodiment, the sensor (e.g., heart sound sensor 526C) can be embedded in implantable medical device 1044, which can be placed in the lumbar region (e.g., for delivering SCS). In various embodiments, each of the one or more activity sensors, the one or more respiratory sensors, the one or more baroreflex sensors, and the one or more additional sensors as discussed in this document (with reference to FIGS. 4, 5, and 9) can be incorporated into lead or lead system 652, included in implantable medical device 1044, or implemented as wearable sensor 1082, that can communicate with implantable medical device 1044 wirelessly via telemetry.

In various embodiments, the pain score as well as other data can be produced by implantable medical device 1044 based on sensed signals and transmitted to portable device 1046 via communication link 648. Portable device 1046 can relay the pain score as well as the other data to network 660 via communication link 658 to be stored, further analyzed, inform the patient's healthcare provider, and/or used to control delivery of one or more pain relief therapies from implantable medical device 1044. When the pain score and/or the other data indicate that the patient needs medical attention, such as when system 1050 is unable to automatically adjust the one or more pain relief therapies for a satisfactory result as indicated by the composite pain score, a notification will be transmitted to medical facility 662 from network 660.

In various embodiments, portable device 1046 and one or more devices within network 660 and/or medical facility 662 can allow a user such as a physician or other caregiver and/or the patient to communicate with implantable medical device 1044, for example to initialize and adjust settings of implantable medical device 1044. For example, the portable device may inform the patient the pain score and/or other information produced by implantable medical device 1044, and allow the patient to turn implantable medical device 1044 on and off and/or adjust certain patient-programmable parameters controlling delivery of a pain-relief therapy.

The sizes and shapes of the elements of system 1050 and their locations relative to the patient's body are illustrated by way of example and not by way of restriction. System 1050 is discussed as a specific application of pain management according to various embodiments of the present subject matter. In various embodiments, the present subject matter may be applied in any type of pain management in monitoring pain, and/or controlling delivery of one or more pain relief energy and/or agents, using one or more implantable and/or wearable devices. In various embodiments, system 1050 can also be implemented without using implantable devices, such as by monitoring pain using only wearable sensors and delivering one or more pain relief energy and/or agents using a wearable device.

Figure 11:
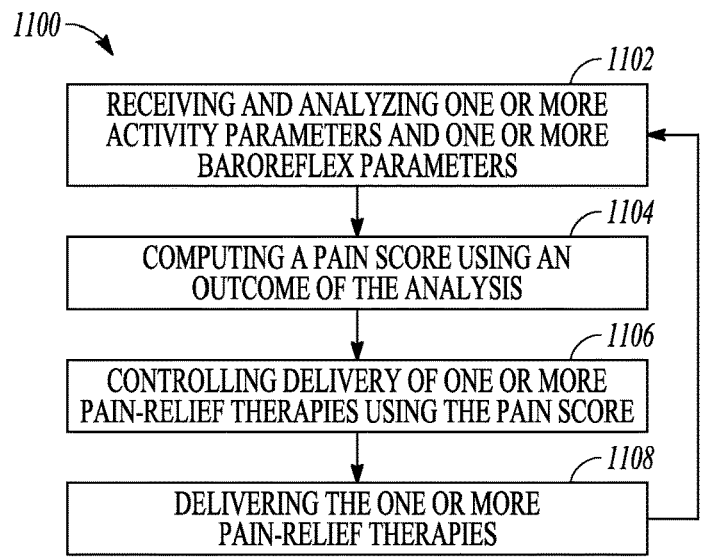
FIG. 11 illustrates another embodiment of a method for pain management.

FIG. 11 illustrates an embodiment of a method 1100 for pain management. In one embodiment, system 200, including the various embodiments of its components, is configured (e.g., programmed) to perform method 1100.

At 1102, one or more activity parameters and one or more baroreflex parameters are received and analyzed. The one or more activity parameters are indicative of a level of physical activity of a patient. The one or more baroreflex parameters allow for determination of BRS of the patient. Examples of the one or more activity parameters and the one or more baroreflex parameters include the parameters that can be generated by parameter generator 932.

At 1104, a pain score is computed using an outcome of the analysis at 702. The pain score is a function of the one or more activity parameters and the one or more baroreflex parameters, and is indicative of a degree (intensity) of the pain.

At 1106, delivery of the one or more pain-relief therapies is controlled using the pain score and therapy parameters. In various embodiments, the one or more activity parameters and the one or more baroreflex parameters are continuously or periodically received and analyzed to update the pain score to provide feedback control on the delivery of the one or more pain-relief therapies.

At 1108, the one or more pain-relief therapies are delivered to the patient. Examples of the one or more pain-relief therapies include those deliverable from pain relief device 206.

Figure 12:
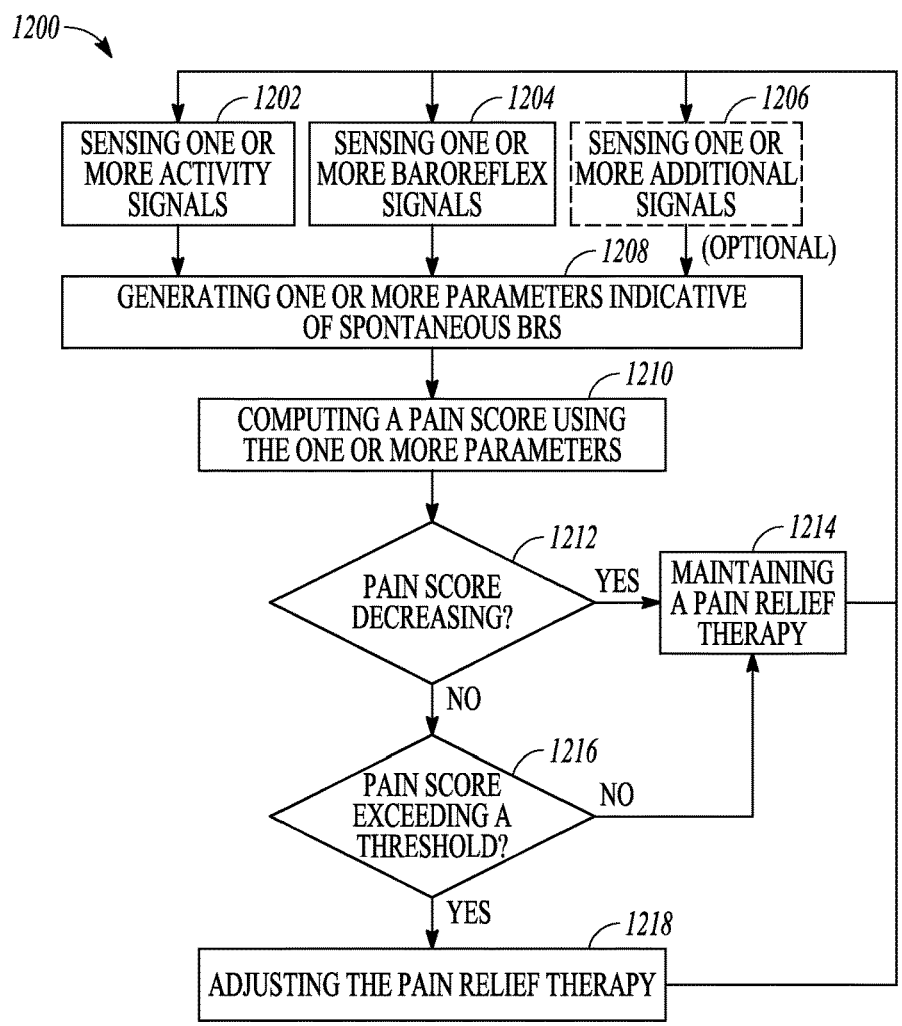
FIG. 12 illustrates another embodiment of a method for pain management.

FIG. 12 illustrates an embodiment of a method 1200 for pain management. In one embodiment, system 200, including the various embodiments of its components, is configured (e.g., programmed) to perform method 1200.

At 1202, one or more activity signals are sensed. Examples of the one or more activity signals include the one or more activity signals that can be sensed using activity sensor(s) 970.

At 1204, one or more baroreflex signals are sensed. Examples of the one or more baroreflex signals include the one or more baroreflex signals that can be sensed using baroreflex sensor(s) 426 or 526.

Optionally at 1206, one or more additional signals are sensed. In various embodiments, the one or more additional signals may be directly indicative of the BRS but otherwise relate to pain. Examples for such one or more additional signals are discussed in U.S. Provisional Patent Application Ser. No. 62/400,336.

At 1208, one or more parameters indicative of spontaneous BRS are generated using the one or more activity signals and the one or more baroreflex signals. Examples of the one or more parameters include the one or more activity parameters and the one or more baroreflex parameters that can be generated using parameter generator 932. In some embodiments, the one or more parameters also include one or more physiological parameters each indicative of a physiological function or state of the patient, one or more functional parameters each indicative of a physical activity or state of the patient, and/or one or more patient parameters including subjective information provided by the patient, in addition to using the one or more activity parameters and the one or more baroreflex parameters, that can be generated using parameter generator 932. In one embodiment, a BRS signal metric is generated using the one or more activity parameters and the one or more baroreflex parameters, and optionally the one or more additional parameters. The BRS signal metric is representative of the BRS of the patient being a function of the level of physical activity of the patient.

At 1210, a pain score is computed using the one or more parameters generated at 808. The pain score is an objective and quantitative measure of a degree (intensity) of pain. In one embodiment, the pain score is computed using the BRS signal metric. In one embodiment, an acute pain score is generated to indicate acute pain, such as around occurrence of an event of interest, and a chronic pain score is also generated to indicate chronic pain.

At 1212, whether the pain score is decreasing (indicating decreasing intensity of pain) is determined. If the pain score is decreasing, delivery of a pain relief therapy is maintained (i.e., the pain relief therapy is not started, stopped, or adjusted in response) at 1214. If the pain score is not decreasing, whether the pain score exceeds a specified therapy threshold is determined at 1216. If the pain score does not exceed the specified therapy threshold, the delivery of the pain relief therapy is maintained (i.e., the pain relief therapy is not started, stopped, or adjusted in response) at 1214. If the pain score exceeds the specified therapy threshold, the pain relief therapy is adjusted, such as optimized. In various embodiments, the optimization can include adjusting the therapy parameters towards improving BRS measures (e.g., as indicated by the BRS signal metric or the pain score). In one embodiment, the optimization includes adjusting the therapy parameters to minimizing the value of the pain score (i.e., to minimizing the intensity of the pain). In one embodiment in which the acute pain score is generated at 1210, the adjustment of the pain relief therapy at 1218 can be applied temporarily. In one embodiment, if a history of acute pain occurring upon specific activity level change(s) has been established for the patient (automatically and/or by a physician, other caregiver, and/or the patient), the adjustment of the pain relief therapy at 1218 can be enabled or mandated upon detection of such specific activity level change(s).

In various embodiments, method 1200 is performed continuously for adjusting the pain relief therapy when such therapy is being applied to the patient. In various embodiments, method 1200 is performed periodically for adjusting the pain relief therapy when such therapy is being applied to the patient. In various embodiments, method 1200 is performed in response to a user command entered by the patient or a user such as a physician or other caregiver, such as when the pain intensifies as perceived by the patient.

Figure 13:
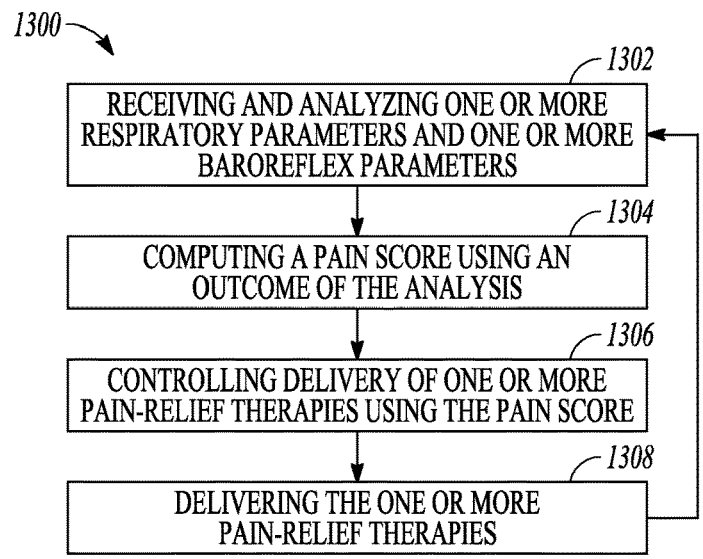
FIG. 13 illustrates another embodiment of a method for pain management.

FIG. 13 illustrates an embodiment of a method 1300 for pain management. In one embodiment, system 200, including the various embodiments of its components, is configured (e.g., programmed) to perform method 1300.

At 1302, one or more respiratory parameters and one or more baroreflex parameters are received and analyzed. The one or more respiratory parameters are indicative of respiratory cycles (each including an inspiratory phase and an expiratory phase) of a patient. The one or more baroreflex parameters allow for determination of BRS of the patient. Examples of the one or more respiratory parameters and the one or more baroreflex parameters include the parameters that can be generated by parameter generator 932.

At 1304, a pain score is computed using an outcome of the analysis at 702. The pain score is a function of the one or more respiratory parameters and the one or more baroreflex parameters, and is indicative of a degree (intensity) of the pain.

At 1306, delivery of the one or more pain-relief therapies is controlled using the pain score and therapy parameters. In various embodiments, the one or more respiratory parameters and the one or more baroreflex parameters are continuously or periodically received and analyzed to update the pain score to provide feedback control on the delivery of the one or more pain-relief therapies.

At 1308, the one or more pain-relief therapies are delivered to the patient. Examples of the one or more pain-relief therapies include those deliverable from pain relief device 206.

Figure 14:
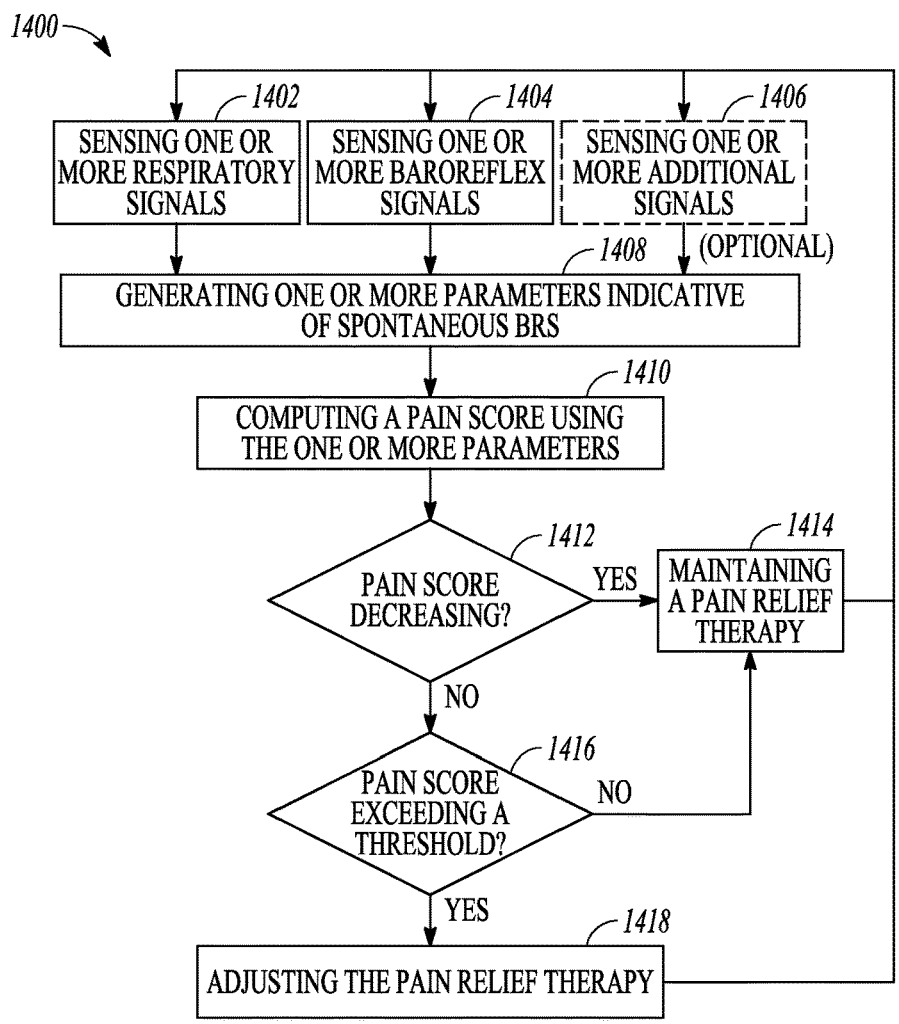
FIG. 14 illustrates another embodiment of a method for pain management.

FIG. 14 illustrates an embodiment of a method 1400 for pain management. In one embodiment, system 200, including the various embodiments of its components, is configured (e.g., programmed) to perform method 1400.

At 1402, one or more respiratory signals are sensed. Examples of the one or more respiratory signals include the one or more respiratory signals that can be sensed using respiratory sensor(s) 526D or 976.

At 1204, one or more baroreflex signals are sensed. Examples of the one or more baroreflex signals include the one or more baroreflex signals that can be sensed using baroreflex sensor(s) 426 or 526.

Optionally at 1406, one or more additional signals are sensed. In various embodiments, the one or more additional signals may be directly indicative of the BRS but otherwise relate to pain. Examples for such one or more additional signals are discussed in U.S. Provisional Patent Application Ser. No. 62/400,336.

At 1408, one or more parameters indicative of BRS are generated using the one or more respiratory signals and the one or more baroreflex signals. Examples of the one or more parameters include the one or more respiratory parameters and the one or more baroreflex parameters that can be generated using parameter generator 932. In some embodiments, the one or more parameters also include one or more physiological parameters each indicative of a physiological function or state of the patient, one or more functional parameters each indicative of a physical activity or state of the patient, and/or one or more patient parameters including subjective information provided by the patient, in addition to using the one or more respiratory parameters and the one or more baroreflex parameters, that can be generated using parameter generator 932. In one embodiment, a BRS signal metric is generated using the one or more respiratory parameters and the one or more baroreflex parameters, and optionally the one or more additional parameters. The BRS signal metric is representative of the BRS of the patient being a function of the respiratory cycle the patient.

At 1410, a pain score is computed using the one or more parameters generated at 808. The pain score is an objective and quantitative measure of a degree (intensity) of pain. In one embodiment, the pain score is computed using the BRS signal metric. In one embodiment, an acute pain score is generated to indicate acute pain, such as around occurrence of an event of interest, and a chronic pain score is also generated to indicate chronic pain.

At 1412, whether the pain score is decreasing (indicating decreasing intensity of pain) is determined. If the pain score is decreasing, delivery of a pain relief therapy is maintained (i.e., the pain relief therapy is not started, stopped, or adjusted in response) at 1414. If the pain score is not decreasing, whether the pain score exceeds a specified therapy threshold is determined at 1416. If the pain score does not exceed the specified therapy threshold, the delivery of the pain relief therapy is maintained (i.e., the pain relief therapy is not started, stopped, or adjusted in response) at 1414. If the pain score exceeds the specified therapy threshold, the pain relief therapy is adjusted, such as optimized. In various embodiments, the optimization can include adjusting the therapy parameters towards improving BRS measures (e.g., as indicated by the BRS signal metric or the pain score). In one embodiment, the optimization includes adjusting the therapy parameters to minimizing the value of the pain score (i.e., to minimizing the intensity of the pain). In one embodiment in which the acute pain score is generated at 1410, the adjustment of the pain relief therapy at 1418 can be applied temporarily. In one embodiment, if a history of acute pain occurring upon specific respiratory pattern change(s) has been established for the patient (automatically and/or by a physician, other caregiver, and/or the patient), the adjustment of the pain relief therapy at 1418 can be enabled or mandated upon detection of such specific respiratory pattern change(s).

In various embodiments, method 1400 is performed continuously for adjusting the pain relief therapy when such therapy is being applied to the patient. In various embodiments, method 1400 is performed periodically for adjusting the pain relief therapy when such therapy is being applied to the patient. In various embodiments, method 1400 is performed in response to a user command entered by the patient or a user such as a physician or other caregiver, such as when the pain intensifies as perceived by the patient.

In some embodiments, methods 1100 and 1300 can be combined, i.e., by sensing both the one or more activity signals and the one or more respiratory signals, and generating the one or more parameters indicative of BRS using the one or more activity signals, the one or more respiratory signals, and the one or more baroreflex signals. In some embodiments, methods 1200 and 1400 can be combined, i.e., by sensing both the one or more activity signals and the one or more respiratory signals, and generating the one or more parameters indicative of BRS using the one or more activity signals, the one or more respiratory signals, and the one or more baroreflex signals.

In various embodiments, a pain management system, such as systems 200 or 1050, may include any one or any combination of the physical and functional structures discussed above and/or one or more other physical and functional structures configured to be used to monitor and control pain for a patient. In addition to the Examples discussed in the Summary section above, non-limiting examples 1-25 for pain management using spontaneous BRS are provided as follows:

In Example 1, a system for providing a patient with pain management, may include a pain monitoring circuit. The pain monitoring circuit may include parameter analyzer circuitry and pain score generator circuitry. The parameter analyzer circuitry may be configured to receive and analyze one or more timing parameters and one or more baroreflex parameter. The one or more timing parameters are indicative of time intervals during which the patient's blood pressure and cardiac interval increase simultaneously or decrease simultaneously. The one or more baroreflex parameters allow for determination of spontaneous baroreflex sensitivity (BRS) of the patient during the time intervals. The pain score generator circuitry may be configured to compute a pain score using an outcome of the analysis. The pain score is a function of the spontaneous BRS of the patient during the time intervals and indicative of a degree of pain of the patient.

In Example 2, the subject matter of Example 1 may optionally be configured to further include a pain relief device configured to deliver one or more pain-relief therapies to the patient and a control circuit configured to control the delivery of the one or more pain-relief therapies using the computed pain score.

In Example 3, the subject matter of any one or any combination of Examples 1 and 2 may optionally be configured such that the parameter analyzer circuitry is further configured to generate a BRS signal metric using the one or more timing parameters and the one or more baroreflex parameters, and the pain score generator circuitry is further configured to compute the pain score using the BRS signal metric.

In Example 4, the subject matter of Example 3 may optionally be configured such that the parameter analyzer circuitry is further configured to generate the BRS signal metric using the one or more timing parameters, the one or more baroreflex parameters, and at least one parameter selected from a physiological parameter indicative of a physiological function or state of the patient, a functional parameter indicative of a physical activity or state of the patient, or a patient parameter including subjective information provided by the patient.

In Example 5, the subject matter of any one or any combination of Examples 1 to 4 may optionally be configured such that the parameter analyzer circuitry is further configured to receive and analyze one or more activity parameters of the one or more timing parameters and the one or more baroreflex parameter, and is further configured to determine the spontaneous BRS of the patient as a function of the level of physical activity of the patient. The one or more activity parameters are indicative of a level of physical activity of the patient.

In Example 6, the subject matter of Example 5 may optionally be configured to further include one or more activity sensors configured to sense one or more activity signals indicative of the level of physical activity of the patient, an activity sensing circuit configured to process the one or more activity signals, an activity feature detector configured to detect one or more activity signal features using the processed one or more activity signals, and a parameter generator configured to generate the one or more activity parameters using the detected one or more activity signal features.

In Example 7, the subject matter of any one or any combination of Examples 1 to 6 may optionally be configured such that the parameter analyzer circuitry is further configured to receive and analyze one or more respiratory parameters of the one or more timing parameters and the one or more baroreflex parameter, the one or more respiratory parameters indicative of respiratory cycles of the patient, the respiratory cycles each including an inspiration phase and an expiration phase, and is further configured to determine the spontaneous BRS of the patient using values of the one or more baroreflex parameters during one or more of inspiration phases or expiration phases of the respiratory cycles of the patient.

In Example 8, the subject matter of any one or any combination of Examples 1 to 7 may optionally be configured such that the pain monitoring circuit further includes one or more respiratory sensors configured to sense one or more respiratory signals indicative of the respiratory cycles of the patient, a respiratory sensing circuit configured to process the one or more respiratory signals, a respiratory feature detector configured to detect one or more respiratory signal features using the processed one or more respiratory signals, and a parameter generator configured to generate the one or more respiratory parameters using the detected one or more respiratory signal features.

In Example 9, the subject matter of any one or any combination of Examples 6 and 8 may optionally be configured such that the pain monitoring circuit further includes one or more baroreflex sensors configured to sense one or more baroreflex signals allowing for the determination of the spontaneous BRS, a baroreflex sensing circuit configured to process the sensed one or more baroreflex signals, and a baroreflex feature detector configured to detect one or more baroreflex signal features using the processed one or more baroreflex signals, and the parameter generator is further configured to generate the one or more baroreflex parameters using the detected one or more baroreflex signal features.

In Example 10, the subject matter of Example 9 may optionally be configured such that the parameter generator is further configured to generate a heart rate or a change of the heart rate of the one or more baroreflex parameters.

In Example 11, the subject matter of any one or any combination of Examples 9 and 10 may optionally be configured such that the baroreflex parameter generator is further configured to generate a blood pressure or a change of the blood pressure of the one or more baroreflex parameters. The blood pressure is an actual blood pressure of the patient or a surrogate of the blood pressure of the patient.

In Example 12, the subject matter of Example 11 may optionally be configured such that the baroreflex parameter generator is further configured to generate an amplitude of second heart sounds (S2) or a pulse transit time (PTT) as the surrogate of the blood pressure of the patient.

In Example 13, the subject matter of any one or any combination of Examples 9 to 12 may optionally be configured such that the baroreflex parameter generator is further configured to generate a heart sound parameter of the one or more baroreflex parameters. The heart sound parameter is representative of an amplitude of a heart sound or a time interval associated with the heart sound.

In Example 14, the subject matter of any one or any combination of Examples 9 to 13 may optionally be configured such that the baroreflex parameter generator is further configured to generate a heart rate variability parameter of the one or more baroreflex parameters. The heart rate variability parameter is a measure of heart rate variability of the patient.

In Example 15, the subject matter of any one or any combination of Examples 9 to 14 may optionally be configured such that the baroreflex parameter generator is further configured to generate a neural parameter of the one or more baroreflex parameters. The neural parameter is indicative of neural activities associated relaying information about blood pressure of the patient.

In Example 16, a method for managing pain of a patient is provided. The method may include: receiving and analyzing one or more timing parameters and one or more baroreflex parameter, and computing a pain score using an outcome of the analysis. The one or more timing parameters are indicative of time intervals during which the patient's blood pressure and cardiac interval increase simultaneously or decrease simultaneously. The one or more baroreflex parameters allow for determination of spontaneous baroreflex sensitivity (BRS) of the patient during the time intervals. The pain score is a function of the spontaneous BRS of the patient during the time intervals and indicative of a degree of pain of the patient.

In Example 17, the subject matter of Example 16 may optionally further include: delivering one or more pain-relief therapies to the patient from a pain relief device, and controlling the delivery of the one or more pain-relief therapies using the pain score.

In Example 18, the subject matter of analyzing the one or more timing parameters and the one or more baroreflex parameters as found in any one or any combination of Examples 16 and 17 may optionally further include generating a BRS signal metric using the one or more timing parameters and the one or more baroreflex parameters, and the subject matter of computing the pain score as found in any one or any combination of Examples 16 and 17 may optionally further include computing the pain score using the BRS signal metric.

In Example 19, the subject matter of generating the BRS signal metric as found in Example 18 may optionally further include generating the BRS signal metric using the one or more timing parameters, the one or more baroreflex parameters, and at least one parameter selected from a physiological parameter indicative of a physiological function or state of the patient, a functional parameter indicative of a physical activity or state of the patient, or a patient parameter including subjective information provided by the patient.

In Example 20, the subject matter of any one or any combination of Examples 16 to 19 may optionally further include: sensing one or more activity signals indicative of a level of physical activity of the patient using one or more activity sensors, and generating one or more activity parameters of the one or more timing parameters using the one or more activity signals.

In Example 21, the subject matter of any one or any combination of Examples 16 to 20 may optionally further include: sensing one or more respiratory signals indicative of respiratory cycles of the patient using one or more respiratory sensors, and generating one or more respiratory parameters of the one or more timing parameters using the one or more respiratory signals.

In Example 22, the subject matter of any one or any combination of Examples 16 to 21 may optionally further include: sensing one or more baroreflex signals allowing for the determination of the spontaneous BRS using one or more baroreflex sensors, and generating the one or more baroreflex parameters using the one or more baroreflex signals.

In Example 23, the subject matter of the one or more baroreflex signals as found in Example 22 may optionally further include one or more of a cardiac signal indicative of a heart rate of the patient or a blood pressure signal indicative of a blood pressure of the patient.

In Example 24, the subject matter of the one or more baroreflex parameters as found in Example 23 may optionally further include a parameter indicative of one or more of a heart rate, a change in the heart rate, a slope of change in the heart rate, or a heart rate variability.

In Example 25, the subject matter of the one or more baroreflex parameters as found in Example 23 may optionally further include a blood pressure parameter, a change in the blood pressure parameter, a slope of the change in the blood pressure parameter, or a measure of a neural activity driven by the blood pressure or the change in the blood pressure, the blood pressure parameter indicative of the blood pressure of the patient.

CONCLUSION

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for providing a patient with pain management, the system comprising:
    a pain monitoring circuit including:
        parameter analyzer circuitry configured to receive and analyze one or more timing parameters and one or more baroreflex parameters allowing for determination of baroreflex sensitivity (BRS) of the patient, the one or more timing parameters indicative of time intervals during which values of the one or more baroreflex parameters are used to determine the BRS and including at least one of a posture parameter or an activity parameter, the posture parameter indicative of a posture of the patient, the activity parameter indicative of a level of physical activity of the patient; and
        pain score generator circuitry configured to compute a pain score using an outcome of the analysis, the pain score being a function of the BRS during the time intervals and indicative of a degree of pain of the patient;
    a pain relief device configured to deliver one or more pain-relief therapies to the patient; and
    a control circuit configured to control the delivery of the one or more pain-relief therapies using the computed pain score.

2. The system of claim 1, wherein the parameter analyzer circuitry is further configured to generate a BRS signal metric using the one or more timing parameters and the one or more baroreflex parameters, and the pain score generator circuitry is further configured to compute the pain score using the BRS signal metric.

3. The system of claim 1, wherein the pain monitoring circuit further comprises:
    one or more baroreflex sensors configured to sense one or more baroreflex signals allowing for the determination of the BRS; and
    a parameter generator configured to generate the one or more baroreflex parameters using the one or more timing parameters and the one or more baroreflex signals.

4. The system of claim 3, wherein the parameter analyzer circuitry is further configured to receive and analyze the posture parameter and the one or more baroreflex parameter and is further configured to determine the BRS of the patient as a function of the posture of the patient.

5. The system of claim 4, wherein the posture parameter is indicative of one or more of a type, a magnitude, a duration, a velocity, or an acceleration of a change in the posture of the patient, and the parameter analyzer circuitry is further configured to generate the BRS signal metric representative of the BRS of the patient being a function of the one or more of the type, the magnitude, the duration, the velocity, or the acceleration of the change in the posture of the patient.

6. The system of claim 3, wherein the parameter analyzer circuitry is further configured to receive and analyze the activity parameter and the one or more baroreflex parameter and is further configured to determine the BRS of the patient as a function of the level of physical activity of the patient.

7. The system of claim 3, wherein the parameter analyzer circuitry is further configured to receive and analyze one or more respiratory parameters of the one or more timing parameters and the one or more baroreflex parameter, the one or more respiratory parameters indicative of respiratory cycles of the patient, the respiratory cycles each including an inspiration phase and an expiration phase, and is further configured to determine the BRS of the patient using values of the one or more baroreflex parameters during one or more of inspiration phases or expiration phases of the respiratory cycles of the patient.

8. The system of claim 3, wherein the one or more baroreflex sensors are further configured to sense at least a cardiac signal of the one or more baroreflex signals, the cardiac signal indicative of cardiac electrical activities of the patient, and the baroreflex parameter generator is further configured to generate one or more of a heart rate, a change in the heart rate, a slope of the change in the heart rate, or a heart rate variability.

9. The system of claim 3, wherein the one or more baroreflex sensors are further configured to sense at least a blood pressure signal of the one or more baroreflex signals, the blood pressure signal indicative of a blood pressure or physiological activities driven by the blood pressure or a change in the blood pressure of the patient, and the baroreflex parameter generator is further configured to generate one or more of a blood pressure parameter, a change in the blood pressure parameter, a slope of the change in the blood pressure parameter, or a measure of a neural activity driven by the blood pressure or the change in the blood pressure, the blood pressure parameter being an actual blood pressure or a surrogate of the blood pressure of the patient.

10. A method for managing pain of a patient, comprising:
receiving and analyzing one or more timing parameters and one or more baroreflex parameters allowing for determination of baroreflex sensitivity (BRS) of the patient, the one or more timing parameters indicative of time intervals during which values of the one or more baroreflex parameters are used to determine the BRS and including at least one of a posture parameter or an activity parameter, the posture parameter indicative of a posture of the patient, the activity parameter indicative of a level of physical activity of the patient;
computing a pain score using an outcome of the analysis, the pain score being a function of the BRS during the time intervals and indicative of a degree of pain of the patient;
delivering one or more pain-relief therapies to the patient from a pain relief device; and
controlling the delivery of the one or more pain-relief therapies using the pain score.

11. The method of claim 10, wherein analyzing the one or more timing parameters and the one or more baroreflex parameters comprises generating a BRS signal metric using the one or more timing parameters and the one or more baroreflex parameters, and computing the pain score comprises computing the pain score using the BRS signal metric.

12. The method of claim 10, further comprising:
sensing a posture signal indicative of the posture of the patient using a posture sensor; and
generating the posture parameter using the posture signal.

13. The method of claim 10, further comprising:
sensing an activity signal indicative of the level of physical activity of the patient using an activity sensor; and
generating the activity parameter using the activity signal.

14. The method of claim 10, further comprising:
sensing one or more respiratory signals indicative of respiratory cycles of the patient using one or more respiratory sensors; and
generating one or more respiratory parameters of the one or more timing parameters using the one or more respiratory signals.

15. The method of claim 10, further comprising:
sensing one or more baroreflex signals allowing for the determination of the BRS using one or more baroreflex sensors; and
generating the one or more baroreflex parameters using the one or more baroreflex signals.

16. The method of claim 15, wherein sensing the one or more baroreflex signals comprises sensing one or more of a cardiac signal indicative of a heart rate of the patient or a blood pressure signal indicative of a blood pressure of the patient.

17. The method of claim 16, wherein generating the one or more baroreflex parameters comprises generating a parameter indicative of one or more of a heart rate, a change in the heart rate, a slope of change in the heart rate, or a heart rate variability.

18. The method of claim 16, wherein generating the one or more baroreflex parameters comprises generating a blood pressure parameter, a change in the blood pressure parameter, a slope of the change in the blood pressure parameter, or a measure of a neural activity driven by the blood pressure or the change in the blood pressure, the blood pressure parameter indicative of the blood pressure of the patient.

19. A non-transitory computer-readable storage medium including instructions, which when executed by a system, cause the system to perform a method for managing pain of a patient, the method comprising:
receiving and analyzing one or more timing parameters and one or more baroreflex parameters allowing for determination of baroreflex sensitivity (BRS) of the patient, the one or more timing parameters indicative of time intervals during which values of the one or more baroreflex parameters are used to determine the BRS and including at least one of a posture parameter indicative of a posture of the patient or an activity parameter indicative of a level of physical activity of the patient;
computing a pain score using an outcome of the analysis, the pain score being a function of the BRS during the time intervals and indicative of a degree of pain of the patient;
delivering one or more pain-relief therapies to the patient from a pain relief device; and
controlling the delivery of the one or more pain-relief therapies using the pain score.

20. The non-transitory computer-readable storage medium of claim 19, wherein the one or more baroreflex parameters comprise at least one of a blood pressure parameter, a change in the blood pressure parameter, a slope of the change in the blood pressure parameter, or a measure of a neural activity driven by the blood pressure or the change in the blood pressure, the blood pressure parameter indicative of a blood pressure of the patient.

* * * * *